(12) United States Patent
Ding et al.

(10) Patent No.: US 8,273,297 B2
(45) Date of Patent: Sep. 25, 2012

(54) PARTICLE AGGLUTINATION IN A TIP

(75) Inventors: Zhong Ding, Pittsford, NY (US); Amy M. Wilson-Colley, Rochester, NY (US)

(73) Assignee: Ortho-Clinical Diagnostics, Inc., Rochester, NY (US)

( * ) Notice: Subject to any disclaimer, the term of this patent is extended or adjusted under 35 U.S.C. 154(b) by 0 days.

(21) Appl. No.: 13/279,923

(22) Filed: Oct. 24, 2011

(65) Prior Publication Data
US 2012/0040446 A1    Feb. 16, 2012

Related U.S. Application Data

(60) Continuation of application No. 12/953,664, filed on Nov. 24, 2010, now Pat. No. 8,048,376, which is a division of application No. 12/046,037, filed on Mar. 11, 2008, now Pat. No. 7,850,917.

(51) Int. Cl.
*G01N 21/00* (2006.01)

(52) U.S. Cl. ...... 422/82.05; 422/50; 422/408; 422/68.1; 422/81; 435/7.1; 435/283.1; 435/287.1; 435/288.7; 436/518; 436/524; 436/536; 436/164; 436/172; 436/174; 436/180

(58) Field of Classification Search ............ 422/50, 422/408, 68.1, 82.05, 81; 435/7.1, 283.1, 435/287.1, 288.7; 436/518, 524, 528, 536, 436/164, 172, 174, 180
See application file for complete search history.

(56) References Cited

U.S. PATENT DOCUMENTS

| | | | |
|---|---|---|---|
| 4,087,248 A | 5/1978 | Miles | |
| 4,305,721 A | 12/1981 | Bernstein | |
| 4,590,157 A | 5/1986 | Chandler et al. | |
| 4,775,515 A | 10/1988 | Cottingham | |
| 4,960,566 A | 10/1990 | Mochida | |
| 4,963,498 A | 10/1990 | Hillman et al. | |
| 5,019,351 A | 5/1991 | Schultz | |
| 5,114,162 A * | 5/1992 | Ditcher | 277/605 |
| 5,144,139 A | 9/1992 | Hillman et al. | |
| 5,174,162 A * | 12/1992 | Miyake et al. | 73/864.21 |
| 5,192,511 A | 3/1993 | Roach | |

(Continued)

FOREIGN PATENT DOCUMENTS

EP    212314    3/1987

(Continued)

OTHER PUBLICATIONS

Milton T. W. Hearn, Carbonyldiimidazole-Mediated Immobilization of Enzymes and Affinity Ligands, methods of Enzymology, Copyright 1987, pp. 102-117 (16 pages), vol. 135.

(Continued)

*Primary Examiner* — Melanie J Yu
(74) *Attorney, Agent, or Firm* — Hiscock & Barclay, LLP

(57) ABSTRACT

An apparatus and a related method for performing particle agglutination reactions in at least one disposable probe tip are disclosed. The at least one probe tip includes a sample cavity for sample acquisition, at least one flanking cavity for the capture of particles by centrifugation or other means, a transition zone for the mixing of the sample with reagents for agglutination and a detection zone for the optical detection of particle agglutination. A mechanism may be attached to the probe tip for the controlled movement of fluids through the internal volume of the probe tip. The probe tip is particularly useful for the automation of high-throughput agglutination-type assays.

12 Claims, 15 Drawing Sheets

U.S. PATENT DOCUMENTS

| | | | |
|---|---|---|---|
| 5,256,376 A | | 10/1993 | Callan et al. |
| 5,338,689 A | | 8/1994 | Yves et al. |
| 5,491,067 A | * | 2/1996 | Setcavage et al. ............ 435/7.25 |
| 5,552,064 A | | 9/1996 | Chachowski et al. |
| 5,593,893 A | * | 1/1997 | Kobashi et al. ................. 436/50 |
| 5,650,068 A | | 7/1997 | Chachowski et al. |
| 5,665,558 A | | 9/1997 | Frame et al. |
| 5,773,305 A | * | 6/1998 | Zabetakis et al. ............. 436/179 |
| 5,891,740 A | | 4/1999 | Di Cesare et al. |
| 5,942,442 A | | 8/1999 | Di Cesare et al. |
| 5,976,896 A | | 11/1999 | Kumar et al. |
| 6,100,079 A | | 8/2000 | Tajima |
| 6,218,193 B1 | | 4/2001 | Kraft et al. |
| 6,261,847 B1 | | 7/2001 | Eherts et al. |
| 6,326,155 B1 | | 12/2001 | Maclennan et al. |
| 6,375,817 B1 | | 4/2002 | Taylor et al. |
| 6,517,778 B1 | | 2/2003 | Kumar et al. |
| 6,579,497 B2 | | 6/2003 | Woodward |
| 6,596,546 B1 | | 7/2003 | Jolley et al. |
| 6,641,993 B1 | | 11/2003 | Jacobs et al. |
| 6,979,534 B1 | * | 12/2005 | Siegel .............................. 435/5 |
| 7,217,561 B2 | | 5/2007 | Winx-Speetjens |
| 2002/0076826 A1 | | 6/2002 | Jacobs et al. |
| 2002/0081747 A1 | * | 6/2002 | Jacobs et al. .................. 436/174 |
| 2003/0007897 A1 | | 1/2003 | Creasey |
| 2003/0022382 A1 | | 1/2003 | Negersmith |
| 2004/0231438 A1 | | 11/2004 | Schwartz |
| 2004/0259268 A1 | | 12/2004 | Jacobs et al. |
| 2005/0048519 A1 | | 3/2005 | Chien et al. |
| 2005/0181519 A1 | * | 8/2005 | Karg et al. ..................... 436/180 |
| 2006/0194342 A1 | | 8/2006 | Bond et al. |
| 2007/0054405 A1 | | 3/2007 | Jacobs et al. |

FOREIGN PATENT DOCUMENTS

| | | |
|---|---|---|
| EP | 0 272 915 A2 | 6/1988 |
| EP | 340562 | 11/1989 |
| EP | 483117 | 4/1992 |
| EP | 542655 | 5/1993 |
| EP | 1 526 370 A2 | 4/2005 |
| JP | 58073866 | 5/1983 |
| JP | 62240843 | 10/1987 |
| JP | 2005164330 | 6/2005 |
| WO | WO 8801374 | 2/1988 |
| WO | WO 9009596 | 8/1990 |
| WO | WO 9417212 | 8/1994 |
| WO | WO 9935497 | 7/1999 |
| WO | WO 2004083859 | 9/2004 |
| WO | WO 2005090970 | 9/2005 |
| WO | WO 2006046054 | 5/2006 |

OTHER PUBLICATIONS

Partial International Search Report for PCT Application No. PCT/US2009/035813; mailed Dec. 4, 2009; 5 pages.

* cited by examiner

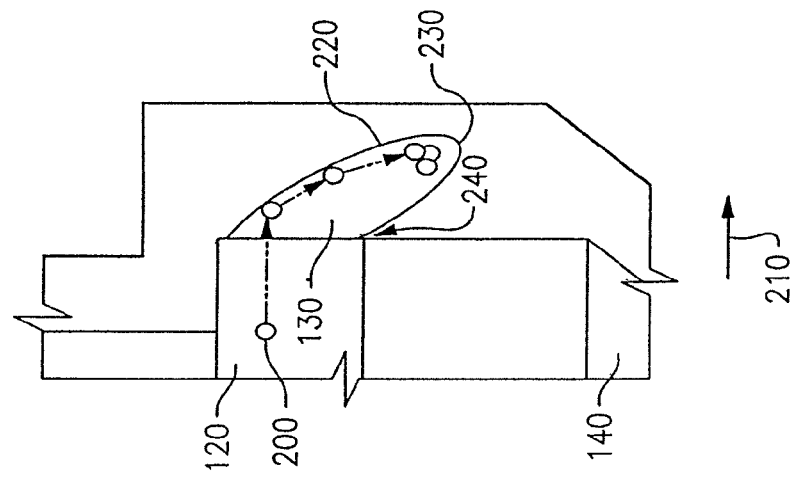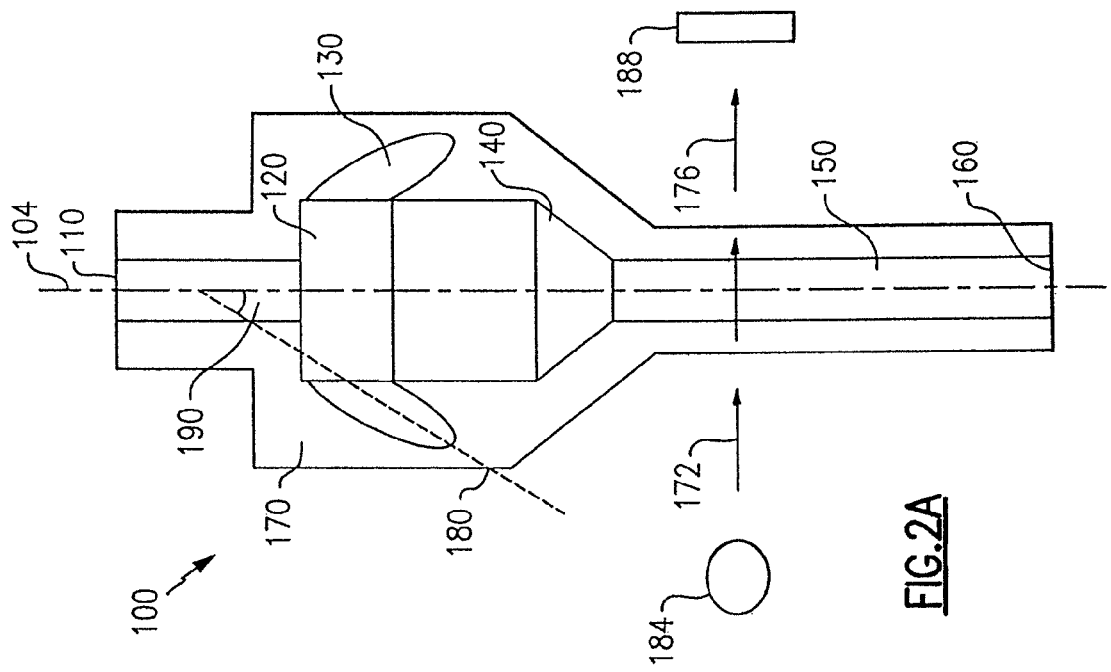

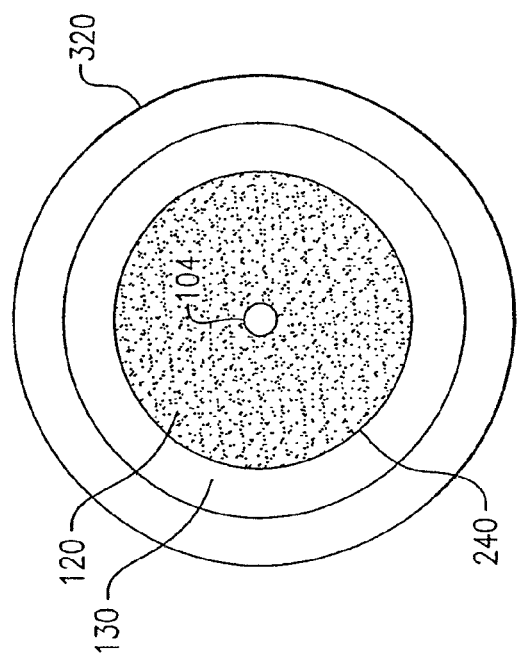
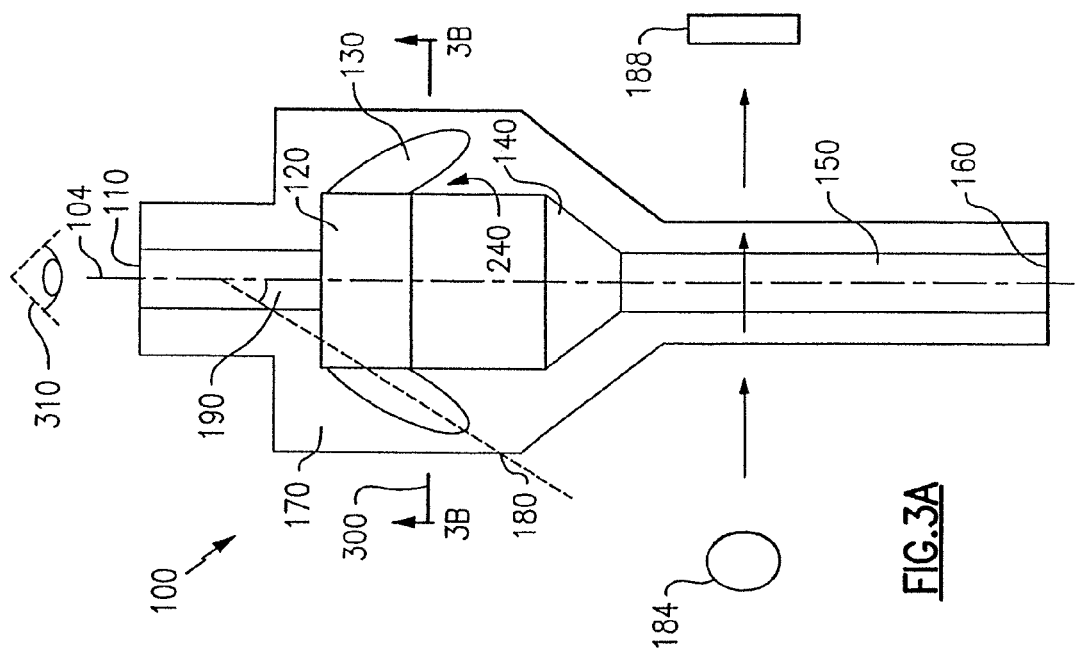
FIG.3B
FIG.3A

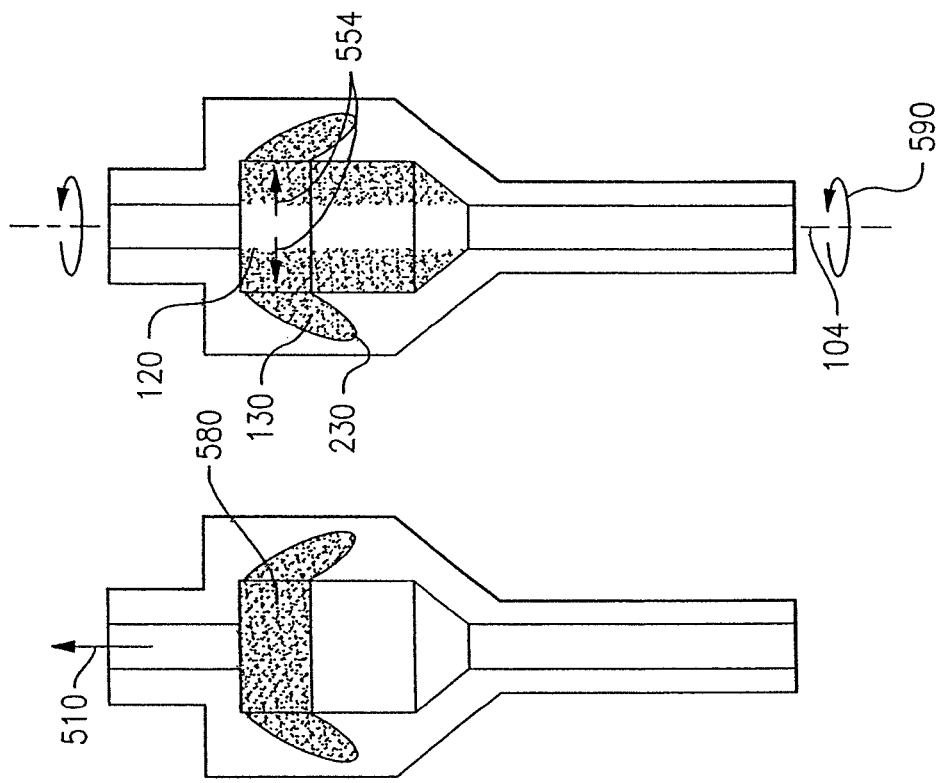
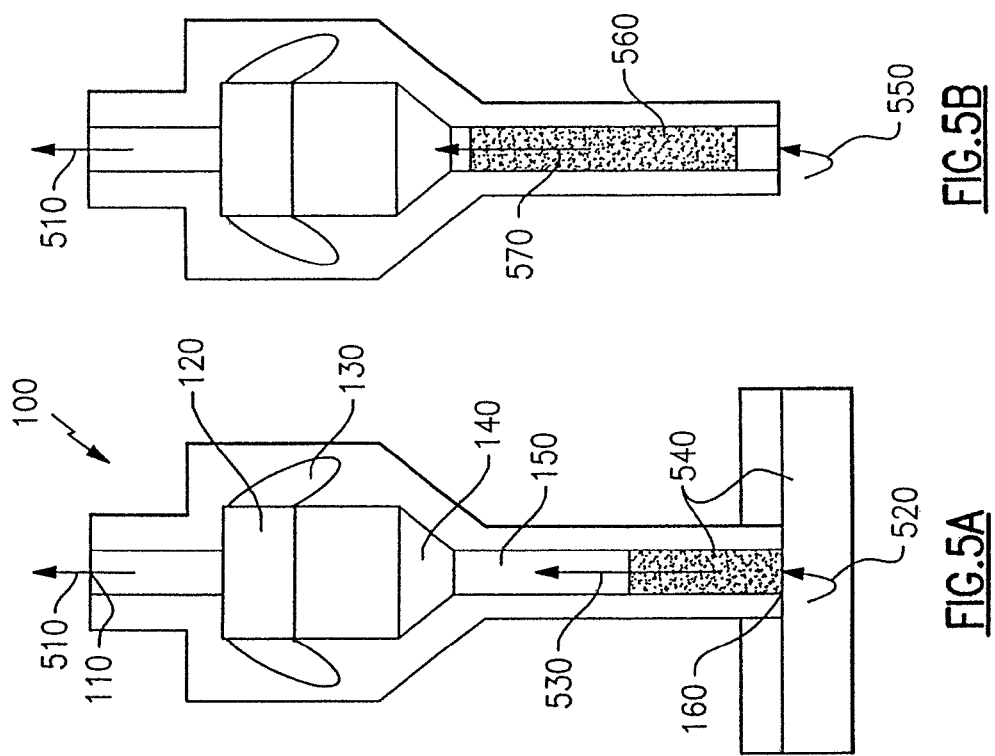

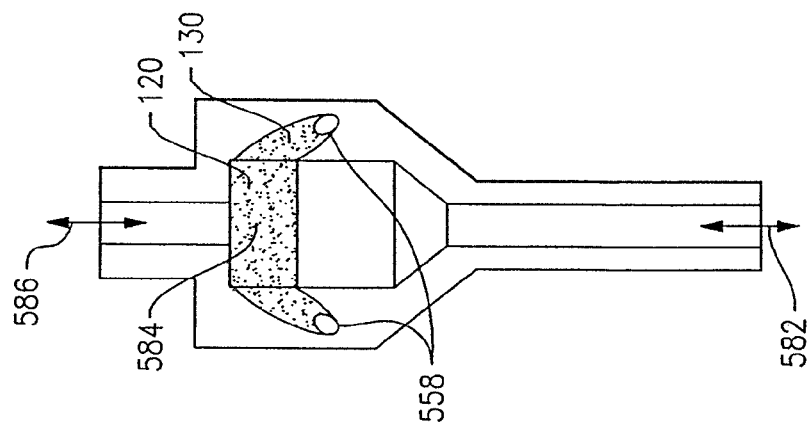
FIG.5H
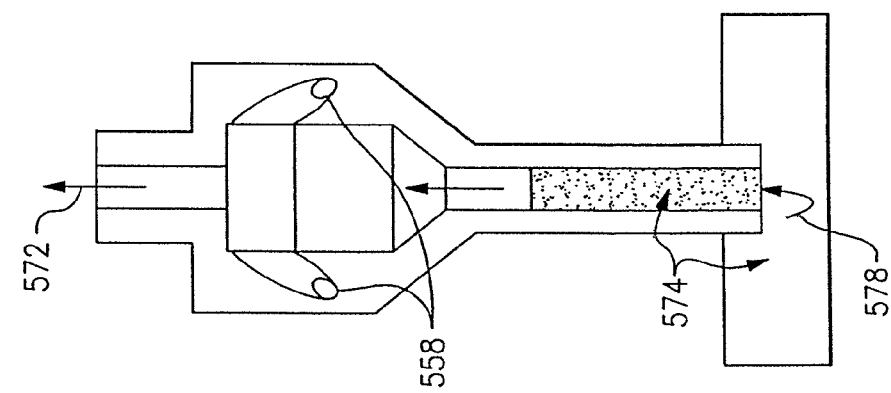
FIG.5G
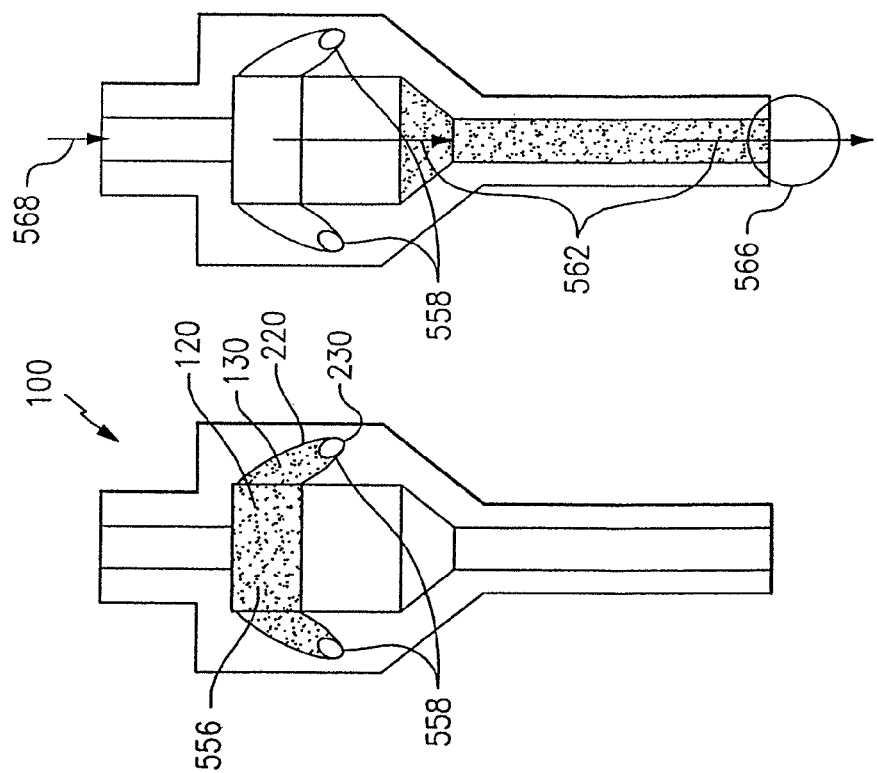
FIG.5F
FIG.5E

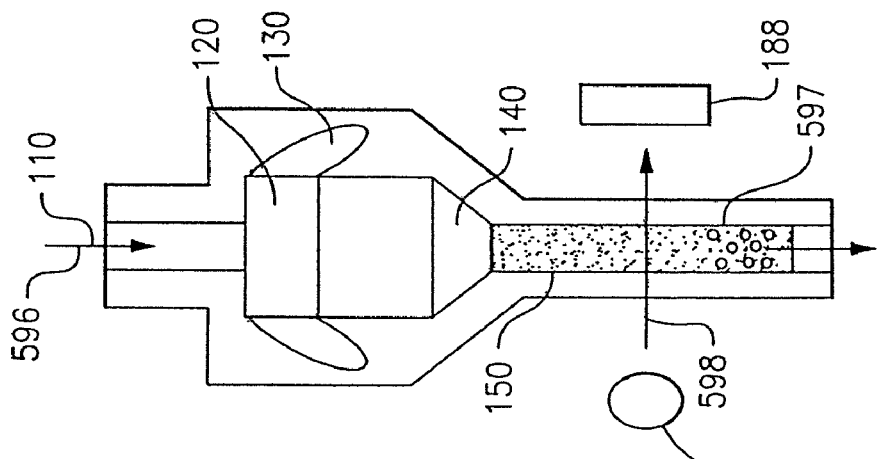
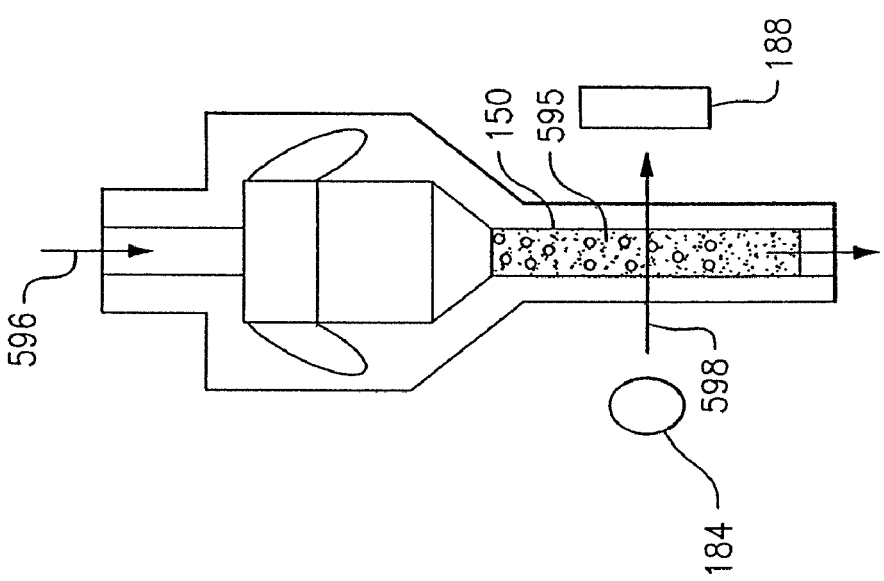
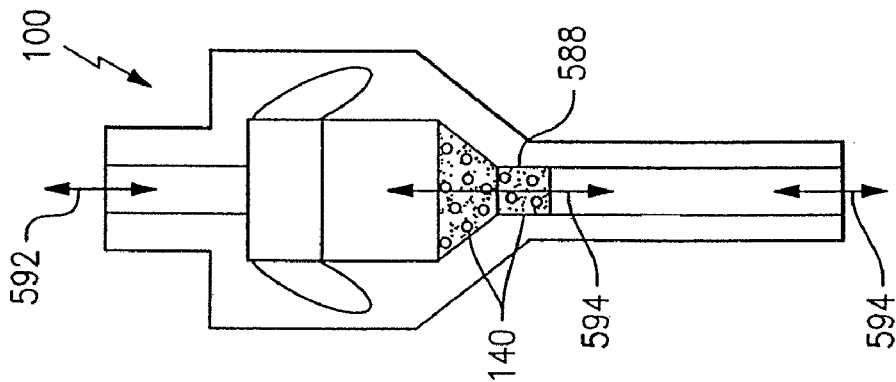

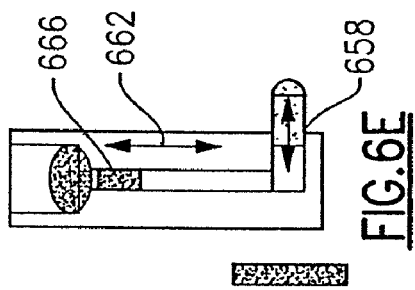
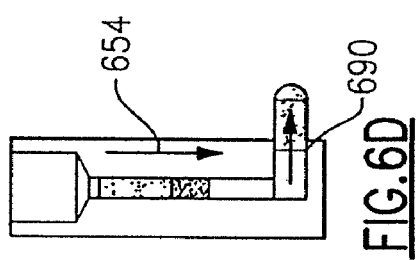
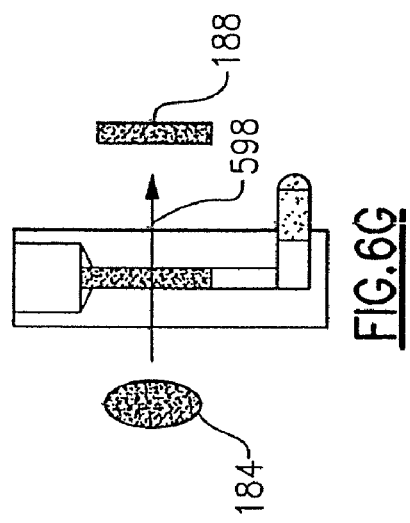
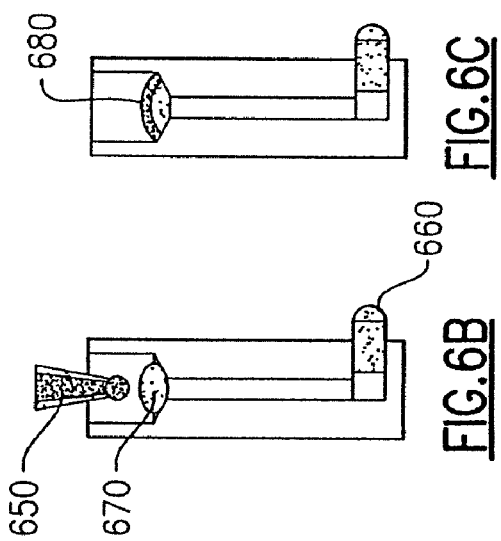
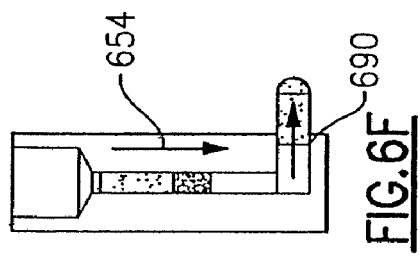
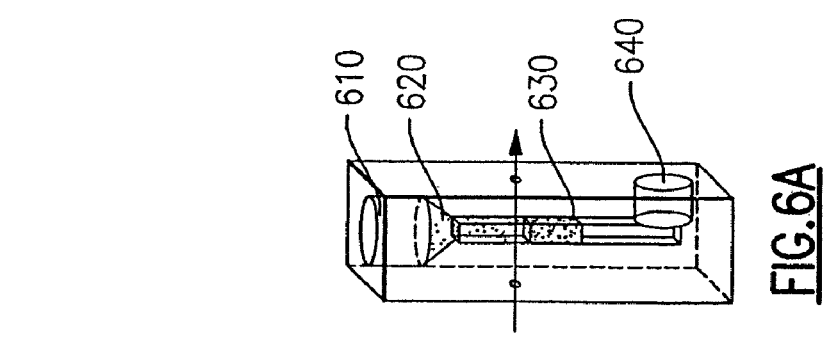

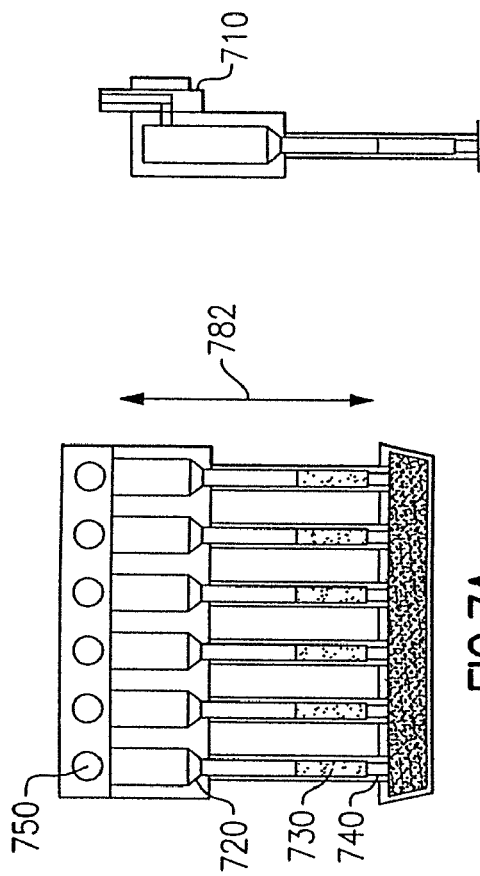
FIG.7A
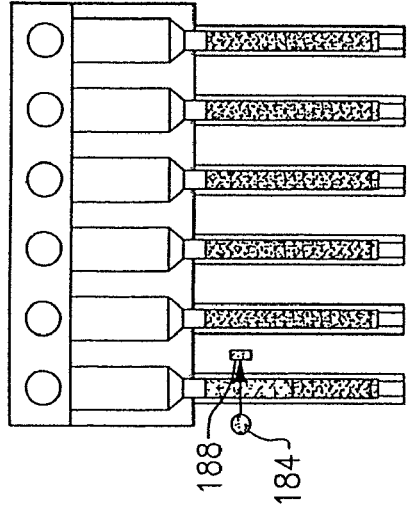
FIG.7B
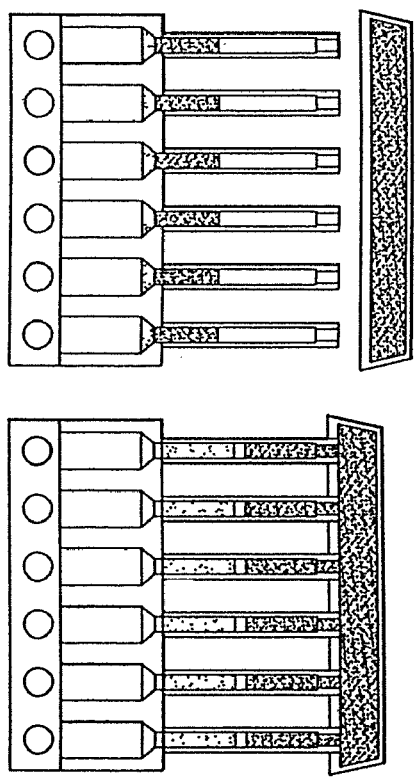
FIG.7C
FIG.7D
FIG.7E

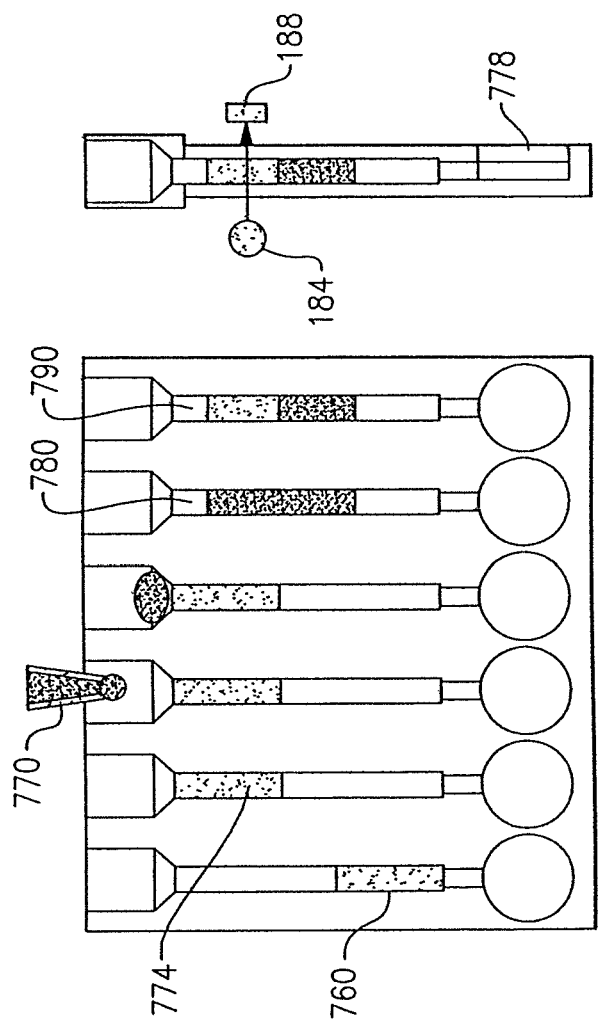
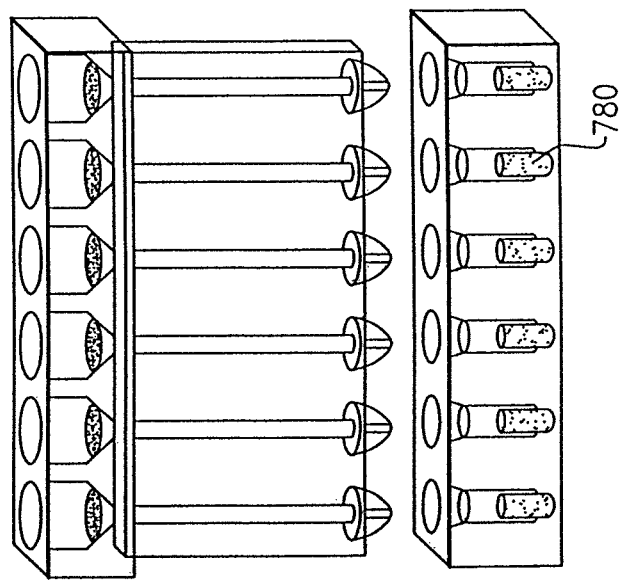
FIG.7G
FIG.7F

PARTICLE AGGLUTINATION IN A TIP

CROSS REFERENCE TO RELATED APPLICATION

This application is a continuation application of U.S. Ser. No. 12/953,664, filed Nov. 24, 2010, now U.S. Pat. No. 8,048,376, which is a divisional application of U.S. Ser. No. 12/046,037, filed on Mar. 11, 2008, now U.S. Pat. No. 7,850,917, the entire contents of each incorporated herein by reference.

FIELD OF THE APPLICATION

The application relates to an apparatus and a method for the rapid detection of the presence or absence of particle agglutination within at least one disposable tip element.

BACKGROUND OF THE INVENTION

Diagnostic assays based upon the interaction of a ligand and a ligand-binding molecule are well known in the art and are widely used in clinical laboratories to detect a variety of antigens or antibodies within a biological sample. Historically, agglutination assays provided a simple way of detecting the specific interaction between an antigen and an antibody through the formation and precipitation of large immunocomplex structures.

Cells in general, and red blood cells in particular, are also amenable to a variety of agglutination methods. Conventional blood typing tests such as the direct and indirect Coomb's tests rely on the agglutination of red blood cells to determine blood group compatibility or to diagnose serious auto-immune diseases such as hemolytic anemia.

The direct Coomb's test or direct anti-globulin test, is used to detect antibodies or complement system factors bound to the surface antigens of a patient's red blood cells in vivo. In a positive Coomb's test, the addition of rabbit anti-human antibody (Coomb's reagent) to a patient's red blood cells bound by human antibody results in agglutination and precipitation of the red blood cells and is thereby indicative of autoimmune hemolytic anemia.

In the indirect Coomb's test or indirect anti-globulin test, the patient's serum is incubated with the red blood cells of a potential donor. If antibodies in the patients serum are bound to the donor's red blood cells, addition of Coomb's reagent results in agglutination and precipitation of the donor's red blood cells and thereby indicates an incapability between the patient and the potential donor's blood. Conversely, the absence of agglutination indicates that the antibodies in the patient's serum do not recognize the surface antigens on the donor's red blood cells. The donor's blood is therefore compatible and can be used for a blood transfusion.

Agglutination immunoassays while simple and cost-effective often lack the required sensitivity for the detection of minute amounts of antigen and are also prone to subjectivity in the interpretation of the results. More recently, an agglutination-type assay with increased sensitivity and reproducibility was achieved by attaching antibodies to sub-micron sized polystyrene microspheres, often called "uniform latex particles". These Brownian particles significantly improved detection sensitivity, because of the increase in scattered light when aggregation between grafted colloids takes place. These improvements to agglutination immunoassays have led to a rapid expansion of commercially available diagnostic kits for the detection of a wide variety of disease-related antigens. Cell-based agglutination assays such as the Coomb's assay or simplified blood typing methods such as the ID-Micro Typing System, Inc., disclosed in U.S. Pat. No. 5,338,689 (Stiftung fur diagnostische Forschung), continue to provide a valuable clinical diagnostic tool especially in view of the growing demand for blood transfusions and the requirement for rapid assessment of blood types for blood transfusions in urgent care facilities.

Despite the improvements over the years, agglutination type assays, and cell-based agglutination type assays in particular, remain laborious and cumbersome because of the need for multiple washing steps and the sequential addition of reagents as dictated by the experimental protocol. Hence, these assays are not easily automated. The handling of large numbers of human patient samples, for example blood samples, also increases the risk of experimental error, reproducibility, contamination and infection of laboratory personnel with human pathogens such as HIV and hepatitis viruses B and C.

Information relevant to attempts to address these problems can be found in U.S. Pat. Nos. 4,087,248; 4,590,157; 4,775,515; 4,960,566; 4,963,498; 5,019,351; 5,144,139; 5,174,162; 5,891,740; 5,942,442; 5,976,896; 6,218,193; 6,261,847; 6,375,817; 6,517,778; the U.S. Patent Application Publication Nos. US 2003/0022382; US 2005/0048519; US 2006/0194342, the International PCT Applications Nos. PCT/US87/02054; PCT/US94/01182; PCT/GB 1999/000052; PCT/GB2005/004166; PCT/EP2005/001029; PCT/GB 1990/000202, the European patent documents EP 212314, EP 340562, EP 483117; EP 542655 and the Japanese patent documents JP 58073866, JP 62240843 and JP 2005164330. Each one of these references suffers, however, from one or more of the following disadvantages: Particle agglutination reactions requiring the repeated intervention of lab personnel, the absence of the description of a device in which all the steps required in a particle agglutination reaction can occur, the absence of automation of multiple particle agglutination reactions using such a device and the absence of a means to detect a particle agglutination reaction in such a device.

For the foregoing reasons, there is an unmet need in the art to implement the automation of particle agglutination type assays so they require minimal interaction with the operator and thereby improve the safety, reliability, cost-effectiveness and efficiency of these important clinical assays.

SUMMARY OF THE APPLICATION

A method is described for performing all the steps required of a particle agglutination reaction in one or more disposable probe tips. The invention further pertains to an apparatus for the visual detection of particle agglutination within a plurality of probe tips.

According to one aspect, a probe tip is used for performing a visually detectable agglutination reaction after aspiration of reagents and a sample into the tip. The probe tip comprises a first port configured to permit negative or positive pressure to the internal volume of the probe tip. The internal volume of the probe tip comprises (a) a sample cavity in fluid communication with the first port (b) at least one flanking cavity configured to capture particles in the sample after separation of the particles from the remainder of the sample, wherein the flanking cavity is in fluid communication with the sample cavity; (c) a detection cavity configured for the detection of agglutinated particles within the sample, wherein the detection cavity is in fluid connection with the sample cavity, (d) a transition zone disposed between the sample cavity and the detection cavity, the transition zone being configured for rotational mixing of the sample moving back and forth through the transition zone between the detection zone and the sample cavity through agitation thereof; and (e) a second port in fluid connection with the detection cavity, the second port being configured to permit reagents and sample to be aspirated into or dispensed from the internal volume of the probe tip.

According to another aspect, the sample within the probe tip comprises a cell suspension. In one version, the cell suspension comprises red blood cells, such as a donor's red blood cells, or a patient's serum and a donor's red blood cells.

In another aspect, the sample comprises a ligand-binding molecule such as an antibody or Coomb's reagent.

In another aspect, the particles are microspheres. In one version, the microspheres are bound to ligand-binding molecules, wherein the ligand-binding molecules are antibodies and the particles are cells, such as red blood cells.

In another aspect, the agglutination is hemagglutination.

According to yet another aspect, the vertical axis of the sample cavity and the vertical axis of the at least one flanking cavity form an angle of 45 degrees or less.

In yet another aspect, the separation of the particles from the remainder of the sample results from separation by centrifugation or separation in a magnetic field.

In yet another aspect, the centrifugation results from the rotation of the probe tip around a primary vertical axis of the probe tip.

In yet another aspect, the flanking cavity is configured to permit the resuspension of the centrifuged particles with the reagents aspirated into the flanking cavity.

In another aspect, the flanking cavity is configured to permit the flow of the resuspended centrifuged particles into the sample and detection cavities of the probe tip.

In another aspect, the internal diameter of the wall of the sample cavity is larger than the internal diameter of the wall of the detection cavity.

In another aspect, the detection cavity is optically transparent to permit optical detection of agglutination.

In another aspect, the probe tip is made from a material that permits fluorescence detection in the detection cavity.

In another aspect, the walls of the detection cavity are capable of transmitting light at certain pre-determined wavelengths.

According to another version, a probe tip is provided for performing a visually detectable agglutination reaction after aspiration of reagents and sample therein. The probe tip comprises a first port in fluid communication with an internal volume of a probe tip. The internal volume of the tip comprises (a) a sample cavity in fluid communication with the first port; (b) a detection cavity configured for the detection of agglutinated particles within the sample, wherein the detection cavity is in fluid connection with the sample cavity; (c) a transition zone disposed between the sample cavity and the detection cavity, the transition zone being configured for rotational mixing of the sample moving back and forth through the transition zone between the detection zone and the sample cavity through agitation thereof; (d) a second port in fluid connection with the detection cavity, the second port being configured to permit reagents and sample to be aspirated into or dispensed from the internal volume of the probe tip, and (e) a third port in fluid communication with the internal cavities of the probe tip.

In one embodiment of the tip, the third port is laterally disposed in relation to the probe tip.

According to another embodiment, the third port is in fluid communication with a displacement cavity, wherein the displacement cavity is configured to permit negative or positive pressure to the internal volume of the probe tip.

The displacement cavity can include a piston wherein the volume of the displacement cavity changes based upon back and forth movement of the piston in the displacement cavity. This back and forth piston movement within the displacement cavity displaces a column of air that in turn exerts a back and forth force against the sample and the reagents through the transition zone of the probe tip. The movement of the piston can be independent. According to another version, the movement of the piston within the displacement cavity of the tip can be coordinated with the rotation of the displacement cavity within a rotor supporting the probe tip about the axis of the rotor.

According to yet another version, an apparatus is provided for the detection of agglutination reactions within a plurality of probe tips. The apparatus comprises a plurality of holders configured for the placement of a plurality of probe tips, each of the plurality of probe tips comprising (i) a first port configured to permit negative or positive pressure to an internal volume of a probe tip, (ii) a sample cavity in fluid communication with the port, (iii) at least one flanking cavity configured to capture particles in the sample after separation of the particles from the remainder of the sample, wherein the flanking cavity is in fluid communication with the sample cavity; (iv) a detection cavity configured for the detection of agglutinated particles within the sample, wherein the detection cavity is in fluid connection with the sample cavity; (v) a transition zone disposed between the sample cavity and the detection cavity, the transition zone being configured for rotational mixing of the sample moving back and forth through the transition zone between the detection zone and the sample cavity through agitation thereof; and (vi) a second port in fluid connection with the detection cavity, the second port being configured to permit reagents and sample to be aspirated into or dispensed from the internal volume of the probe tip, and a means for separating the particles in the sample from the remainder of the sample.

According to one embodiment, the particles in the sample can be separated from the remainder of the sample by means of centrifugation.

This centrifugation can be accomplished according to one version through the rotation of the probe tip about a primary vertical axis of the probe tip. Alternatively, the particles in the sample can be separated from the remainder of the sample through magnetic means.

According to yet another version, an apparatus is provided for the detection of agglutination reactions within a plurality of probe tips. The apparatus comprises a plurality of holders configured for the placement of a plurality of probe tips, each of the plurality of probe tips comprises (a) a first port in fluid communication with an internal volume of a probe tip, the internal volume comprising (i) a sample cavity in fluid communication with the first port; (ii) a detection cavity configured for the detection of agglutinated particles within the sample, wherein the detection cavity is in fluid connection with the sample cavity; (iii) a transition zone disposed between the sample cavity and the detection cavity, the transition zone being configured for rotational mixing of the sample moving back and forth through the transition zone between the detection zone and the sample cavity through agitation thereof; and (iv) a second port in fluid connection with the detection cavity, the second port being configured to permit reagents and sample to be aspirated into or dispensed from the internal volume of the probe tip, and (v) a third port in fluid communication with the internal cavities of the probe tip.

The third port can be laterally disposed to the probe tip, or alternatively, the third port can be in fluid communication with a displacement cavity wherein the apparatus further includes a piston disposed in relation to the displacement.

In one embodiment, the volume of the displacement cavity changes with the movement of the piston in the displacement cavity wherein the back and forth movement of the piston within the displacement cavity displaces a column of air that in turn exerts a back and forth force against the sample and the reagents through the transition zone of the probe tip.

The movement of the piston can occur by various means. In one version, the movement is through an independent drive mechanism. In another, the drive mechanism is coordinated with the rotation of the displacement cavity within a rotor housing the tip, wherein the tip rotates about the axis of the rotor. The apparatus further comprises means for the detection of agglutination in the probe tips.

According to yet another version, a method is described for performing an agglutination reaction in a single probe tip, the method comprising the steps of (a) providing a probe tip comprising a first port configured to permit negative or positive pressure to an internal volume of a probe tip, the internal volume comprising (i) a sample cavity in fluid communication with the first port; (ii) at least one flanking cavity configured to capture particles in the sample after the separation of the particles from the remainder of the sample, wherein the flanking cavity is in fluid communication with the sample cavity; (iii) a detection cavity configured for the detection of agglutination within the sample, wherein the detection cavity is in fluid connection with the sample cavity; (iv) a transition zone between the sample cavity and the detection cavity, configured for rotational mixing of the sample moving back and forth through the transition zone; and (v) a second port in fluid connection with the detection cavity, the second port configured to permit reagents to be aspirated into or dispensed from the internal volume of the probe tip; (b) aspirating a sample into the sample cavity of the probe tip; (c) separating the particles from the remainder of the sample and capturing the in the at least one flanking cavity of the probe tip; (d) dispensing the sample supernatant from the probe tip; (e) aspirating reagents for agglutination into the probe tip; (f) resuspending the sample pellet from the at least one flanking cavity; and (g) moving the resuspended sample pellet to the detection cavity, wherein agglutination in the resuspended sample pellet is detected in the detection cavity.

According to one version, the sample pellet can be resuspended by rotational mixing at the transition zone of the probe tip. The sample, according to one embodiment, comprises a cell suspension, wherein the cell suspension can comprise red blood cells, a patient's whole blood, and/or a patient's serum and a donor's red blood cells. The reagents for agglutination can comprise a ligand-binding molecule in which the ligand-binding molecule is an antibody. In another embodiment, the reagents for agglutination comprise Coomb's reagent. In another embodiment, the reagents for agglutination comprise microspheres in which the microspheres are bound to ligand-binding molecules. The reagents for agglutination can also comprise red blood cells of known blood group.

In another embodiment, the particles are separated from the remainder of the sample by centrifugation or by separation in a magnetic field.

According to yet another version, a kit is provided for performing visually detectable agglutination reactions in a single probe tip, the kit comprising: (a) a probe tip comprising a first port configured to permit negative or positive pressure to an internal volume of a probe tip, the internal volume comprising (i) a sample cavity in fluid communication with the port; (ii) a flanking cavity configured to capture particles in the sample after separation of the particles from the remainder of the sample, wherein the flanking cavity is in fluid communication with the sample cavity; (iii) a detection cavity configured for the detection of agglutination within the sample, wherein the detection cavity is in fluid connection with the sample cavity; (iv) a transition zone between the sample cavity and the detection cavity, configured for rotational mixing of the sample moving back and forth through the transition zone; and (v) a second port in fluid connection with the detection cavity, the second port configured to permit reagents to be aspirated into or dispensed from the internal volume of the probe tip, and (b) reagents for agglutination. The reagents for agglutination can comprise one or more ligand-binding molecules or microspheres bound by ligand-binding molecules in which the ligand binding molecules are antibodies. In another embodiment, the reagents for agglutination comprise Coomb's reagent. In another embodiment, the reagents for agglutination comprise red blood cells of known blood group.

In another embodiment of the herein described kit, the particles are separated from the remainder of the sample by centrifugation or by separation in a magnetic field.

According to still another version, a kit is provided for performing visually detectable agglutination reactions in a single probe tip, the kit comprising (a) a probe tip comprising a first port in fluid connection with an internal volume of a probe tip, the internal volume comprising (i) a sample cavity in fluid communication with the first port; (ii) a detection cavity configured for the detection of agglutination within the sample, wherein the detection cavity is in fluid connection with the sample cavity; (iii) a transition zone between the sample cavity and the detection cavity, configured for rotational mixing of the sample moving back and forth through the transition zone; (iv) a second port in fluid connection with the detection cavity, the second port configured to permit reagents to be aspirated into or dispensed from the internal volume of the probe tip; (v) a third port in fluid communication with the sample and detection cavities of the tip, and (vi) a displacement cavity in fluid communication with the third port, wherein the displacement cavity has a piston, and (b) reagents for agglutination. The reagents for agglutination comprise one or more ligand-binding molecules or microspheres bound by ligand-binding molecules, wherein the ligand binding molecules include antibodies. The reagents for agglutination can comprise Coomb's reagent or red blood cells of a known blood group.

In another embodiment, the volume of the displacement cavity changes based upon the movement of the piston in the displacement cavity wherein the back and forth movement of the piston within the displacement cavity displaces a column of air that in turn exerts a back and forth force against the sample and the reagents through the transition zone of the probe tip. The movement of the piston can be independent or coordinated with the rotation of the displacement cavity within a rotor about the axis of the rotor.

It should be understood that this application is not limited to the embodiments disclosed in this Summary, and it is intended to cover modifications and variations that are within the scope of those of sufficient skill in the field, and as defined by the claims.

The previously described embodiments have many advantages, including the ability to perform an agglutination reaction in a single probe tip that requires minimal intervention by lab personnel. The reactions are both cost-effective and faster than conventional cartridge methods known in the art. The methods disclosed herein are therefore particularly useful for the automation of high-throughput agglutination-type assays.

BRIEF DESCRIPTION OF THE DRAWINGS

FIG. 2 illustrates an enlarged partial view of the probe tip of FIG. 1 illustrating the capture of separated particles within a flanking cavity thereof;

FIG. 3(a) depicts a cross-section view of the tip of FIGS. 1 and 2;

FIG. 3(b) is a sectioned view of the tip of FIG. 3(a) taken through line 3(b)-3(b);

FIGS. 5(a)-5(k) illustrate sequential cross-sectional views of the probe tip of FIG. 1, representing a method of forming an agglutination reaction in the probe tip;

FIGS. 6(a)-6(g) depict apparatus including a probe tip made in accordance with a second embodiment including a reciprocally driven piston 660, the tip being used for particle agglutination;

FIGS. 7(a)-7(g) depict sectioned elevated views of an apparatus in accordance with a third embodiment for the detection of particle agglutination in multiple probe tips. In FIGS. 7(a)-7(e), negative or positive pressure is applied to the internal volume of the probe tips through a proboscis at the top of each probe tip whereas in FIGS. 7(f)-7(g), the pressure is applied to the bottom of each probe tip using either a piston or deformable membrane;

FIGS. 9(a)-9(e) depict a direct Coomb's test in a probe tip whereas FIGS. 9(c)-9(e) show an indirect Coomb's test in a probe tip.

DETAILED DESCRIPTION

Definitions

Figure 1:
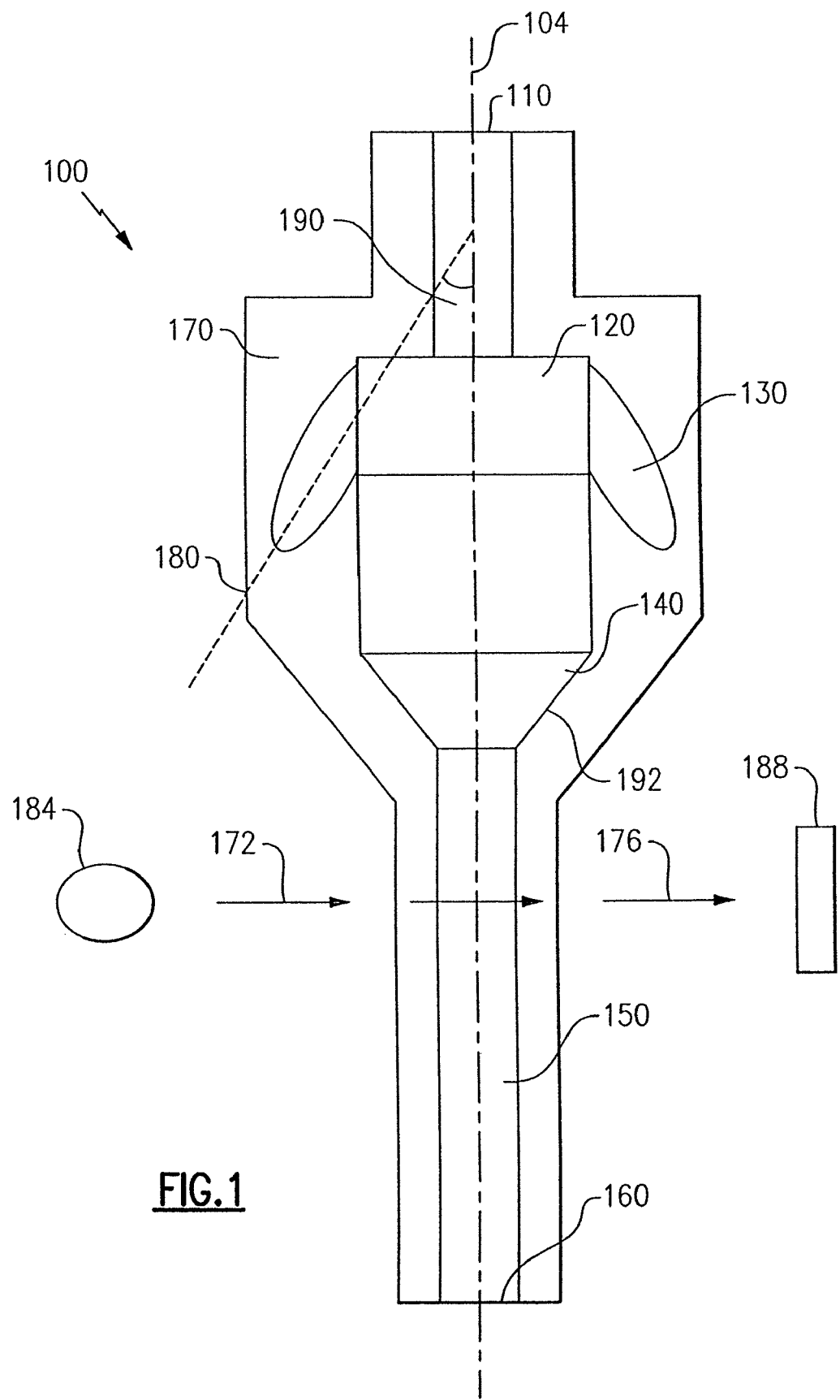
FIG. 1 depicts a cross-sectional view of a probe tip made in accordance with a first embodiment.

Unless defined otherwise, all technical and scientific terms used herein have the same meaning as is commonly understood by one of skill in the art. The following definitions are provided to help interpret the disclosure and claims of this application. In the event a definition in this section is not consistent with definitions elsewhere, the definition set forth in this section will control.

The term "plurality" as used herein refers to a quantity of two or more.

An element is in "fluid communication" with another element when a fluid is able to travel from one element to the other via capillary action and/or gravity. The elements may be in direct contact, but do not need to be in direct contact; i.e., other elements through which said fluid can pass may be intervening. An element is "not in fluid communication" with another element when a fluid is not able to travel from one element to the other via capillary action and/or gravity. Typically, the elements are physically separated, i.e. spaced apart.

As used herein, the term "particle" includes, but is not limited to, any particle used in agglutination assays to which a ligand or ligand-binding molecule may be coupled. Particles may be cells, for example, bacteria or red blood cells or white blood cells. In another embodiment, the particles are made of latex, although other types of particles to which a ligand may be coupled are also included within the scope of the invention. These inert particles may be comprised of any suitable material, such as glass or ceramics or carbon, and/or one or more polymers, such as, for example, nylon, polytetrafluoroethylene (TEFLON™), polystyrene, polyacrylamide, styrene-divinylbenzene polymers such as Sephadex, Sepharose or Sephacryl (sold by Pharmacia AB, Uppsala, Sweden), agarose, cellulose, cellulose derivatives, or dextran, and/or can comprise metals. Porous glass or silica gel particles may also be suitable. Further examples of particles include, but are not limited to, plastic particles, ceramic particles, carbon particles, polystyrene microbeads, glass beads, magnetic beads, hollow glass spheres, metal particles, particles of complex compositions, microfabricated or micromachined particles.

The particle size may be from 0.1 micron to 1000 microns. Preferably, the particle size is from 1 to 200 microns. These particles are generally in the form of beads, beaded gels or microspheres, although they may have any shape. In principle, any ligand may be covalently bound to a solid-phase matrix such as agarose beads (e.g., Sepharose Pharmacia) using known techniques, for example as described by Hearn et al., Methods in Enzymology Vol. 35:102-117 (1987). Generally, the beads are first activated by a chemical agent, such as glutaraldehyde, carbonyldiimidizole, cyanogen bromide hydroxysuccinimide, tosyl chloride or the like. The chosen ligand is then covalently attached to the beads, resulting in an extremely stable linkage of the ligand to the support.

As used herein, a "ligand" is any molecule that is capable of binding to a ligand-binding molecule. In another preferred embodiment, the ligand is exposed on the surface of an analyte as defined herein. In one embodiment, the ligand is an epitope of an antibody. For example, the ligand may be a component of a virus, bacteria or parasite. A ligand may be a surface antigen on a cell such as a red blood cell. A number of ligands are also known that bind immunoglobulin molecules and may be covalently coupled to the particles used in this application, for example Protein A, Protein G, Protein A/G and KappaLock™ (see also U.S. Pat. No. 5,665,558, the contents of which are herein incorporated by reference in its entirety). The ligand may bind to the isotype of the antibody that is used or tested for or, alternatively, one may use a bridging antibody, e.g., an IgG anti-IgM, for an IgM antibody. Thus, an IgG anti-IgM antibody would be coupled to the ligand as a "bridge" and an IgM antibody would bind to the IgG anti-IgM antibody.

The term "ligand-binding", as used herein, refers to a member of a binding pair, i.e., two different molecules wherein one of the molecules specifically binds to the second molecule through chemical or physical means. In addition to antigen and antibody binding pair members, other binding pairs include, as examples without limitation, biotin and avidin, carbohydrates and lectins, complementary nucleotide sequences, complementary peptide sequences, effector and receptor molecules, enzyme cofactors and enzymes, enzyme inhibitors and enzymes, a peptide sequence and an antibody specific for the sequence or the entire protein, polymeric acids and bases, dyes and protein binders, peptides and specific protein binders (e.g., ribonuclease, S-peptide and ribonuclease S-protein), and the like. Furthermore, binding pairs can include members that are analogs of the original binding member, for example, an analyte-analog or a binding member made by recombinant techniques or molecular engineering. If the binding member is an immunoreactant it can be, for example, a monoclonal or polyclonal antibody, a recombinant protein or recombinant antibody, a chimeric antibody, a mixture(s) or fragment(s) of the foregoing, as well as a preparation of such antibodies, peptides and nucleotides for which suitability for use as binding members is well known to those skilled in the art. A ligand-binding member may be a polypeptide affinity ligand (see, for example, U.S. Pat. No. 6,326,155, the contents of which are hereby incorporated by reference herein in its entirety). In one embodiment, the ligand-binding member is labeled. The label may be selected from a fluorescent label, a chemiluminescent label or a bioluminescent label, an enzyme-antibody construct or other similar suitable labels known in the art.

As used herein, the term "antibody" includes both polyclonal and monoclonal antibodies; and may be an intact molecule, a fragment thereof (such as Fv, Fd, Fab, Fab' and F(ab)'2 fragments, or multimers or aggregates of intact molecules and/or fragments; and may occur in nature or be produced, e.g., by immunization, synthesis or genetic engineering.

The antibody or antigen used herein is dependent upon the antibody or antigen that is being tested. For example, the number of blood group antigens and thus, antibodies to these antigens that have been identified is very large, with more antigens and antibodies continually being determined. The International Society of Blood Transfusion has published a non-exclusive list of red cell antigens in Blood Group Terminology 1990, Vox. Sang. 58:152-169 (1990 and includes, but is not limited to, antibodies and antigens A, B, D, C, c, $C^w$, E, e, K, $Fy^a$, $Fy^b$, $Jk^a$, $Jk^b$, S and s.

"Agglutination", as used herein refers to the clumping of a suspension of cellular or particulate antigen by a reagent, usually an antibody or other ligand-binding entity (see, for example, U.S. Pat. Nos. 4,305,721, 5,650,068 and 5,552,064, the contents of which are hereby incorporated herein by reference in their entirety).

"Hemagglutination" refers to the agglutination of red blood cells. Hemagglutination can be used to identify red blood cell surface antigens (with known antibodies) or to screen for antibodies (with red blood cells expressing known surface antigens).

As used herein, the term "sample" refers to a material suspected of containing at least one analyte. The sample can be used directly as obtained from the source or following a pretreatment to modify the character of the sample. The sample can be derived from any biological source, such as a physiological fluid, including, blood, saliva, ocular lens fluid, cerebral spinal fluid, sweat, urine, milk, ascites fluid, raucous, synovial fluid, peritoneal fluid, amniotic fluid or the like. The sample can be pretreated prior to use, such as preparing plasma from blood, diluting viscous fluids, or the like; methods of treatment can involve filtration, distillation, concentration, inactivation of interfering components, and the addition of reagents. Besides physiological fluids, other liquid samples can be used. In addition, a solid material suspected of containing an analyte can be used as the sample. In some instances it may be beneficial to modify a solid sample to form a liquid medium or to release the analyte.

The term "analyte", as used herein, refers to the compound or composition to be detected or measured and which has at least one epitope or binding site or ligand. The analyte can be any substance for which there exists a naturally occurring binding member or for which a binding member can be prepared. Analytes include, but are not limited to, toxins, organic compounds, proteins, peptides, microorganisms (bacteria, viruses or parasites and the like), amino acids, nucleic acids, hormones, steroids, vitamins, drugs, virus particles and metabolites of or antibodies to any of the above substances. The term "analyte" also includes any antigenic substances, haptens, antibodies, macromolecules and combinations thereof. In one embodiment, the analyte is a cell surface antigen. In another embodiment, the analyte is a surface antigen of a red blood cell.

As used herein, "Coomb's reagent" refers to a preparation of antibodies, raised in animals, directed against one of the following human immunoglobulin, complement or a specific immunoglobulin e.g. anti-human IgG for use in the Coomb's test.

As used herein, "centrifugation" refers to the rotation of an object about an axis of rotation. In one exemplary embodiment, centrifugation refers to the rotation of the probe tip around its own primary vertical axis 104 as depicted in FIG. 1.

As used herein, the "probe tip" herein is a device containing one or more internal cavities. In one embodiment, the probe tip is composed of a molded, solid material that can be centrifuged without deformation of the internal cavities. In another embodiment, the material does not promote the adhesion of a biological sample to the internal walls of the probe tip. In another embodiment the probe tip is made out of a plastic material. In an exemplary embodiment, the probe tip is made out of acrylic. In another embodiment, the probe tip is defined by a molded structure having internal cavities in fluid communication with one or more apertures.

As used herein, the term "cavity" refers to any three-dimensional enclosure within the described probe tip. In an exemplary embodiment, one or more cavities are in fluid communication with each other.

As used herein, the "transition zone" refers to a region within the internal cavities of the probe tip where sample and/or reagents are moved by means of a vertical (e.g., up and down) movement of the sample between adjacent chambers within the probe tip in order to promote rotational mixing of contained sample and/or reagents. In one embodiment, the transition zone has a smaller defined inside diameter than that of an adjacent portion of the probe tip through which the sample is moved. Similar "transition zones" are described in U.S. Pat. No. 6,641,993 and the published U.S. Publication Number US 2007/0054405, the contents of which are hereby incorporated herein by reference in their entirety.

As used herein, "cell suspension" refers to a mixture of cells in a liquid. Cells can be eukaryotic or prokaryotic cells. In one embodiment, the cells are bacteria. In another embodiment, the cells are pathogenic bacteria. In a preferred embodiment, the cells are blood cells. In another preferred embodiment, the cells are red blood cells.

As used herein, "red blood cells" (RBCs) used in the application may be isolated from whole blood by centrifugation or through a density gradient such as a Ficoll gradient. In one embodiment, the red blood cells have a hematocrit of 3%, 5%, 10%, 20%, 30% or 40%. In a preferred embodiment, the hematocrit is between 30% to 40%.

As used herein, "to capture" refers to a type of separation in which one or more moieties or sample components is retained in or on one or more areas of a surface, chamber, chip, tube, or any vessel that contains a sample, where the remainder of the sample can be removed from that area. In one embodiment, "to capture" refers to the collection of particles used herein within at least one flanking cavity of the probe tip. In another embodiment, the particles are captured in the at least one flanking cavity of the tip through centrifugation of the probe tip around its own primary vertical axis. In another embodiment, magnetic particles used in the application are captured by means of a magnetic field.

As used herein, "detection" refers to the detection of particle agglutination, typically using a photodetector (see, for example, U.S. Pat. No. 5,256,376 and published U.S. patent application US 2004/0166551, the contents of which are hereby incorporated herein by reference in their entirety). In one embodiment, detection refers to the detection of bioluminescence or chemiluminescence or fluorescence.

As used herein, the term "agitation" refers to the movement of the probe tip that results in the rotational mixing of the sample and/or reagents within the internal cavities of the probe tip. In one embodiment, the agitation is generated by a piston that exerts positive or negative pressure on the internal cavities of the probe tip.

As used herein, the term "piston" refers to any component that can apply negative or positive pressure to the internal volume of a probe tip. In one embodiment, a piston is cylindrical in shape and fits within a channel in such a manner as to slide against the internal wall of the channel in an air-tight manner (i.e., there is no substantial leak of air between the cylindrical surface of the piston and the wall). Movement of the piston confers either a vacuum or pressure to the internal volume of the probe tip and thereby drives the movement of fluids within the internal cavities of a probe tip.

The term "fluorescence detection" refers to the detection of a fluorophore-conjugated ligand or ligand-binding entity (see, for example, U.S. Pat. No. 6,596,546, the contents of which are hereby incorporated herein by reference in its entirety).

As used herein, "transmitting light at certain pre-determined wavelengths" refers to the ability of walls of the probe tip's detection cavity to transmit electromagnetic radiation of a wavelength required for the excitation of a fluorescent ligand and electromagnetic radiation of a wavelength characteristic of the subsequent emission of fluorescence.

The following description relates to certain preferred embodiments of the application, and to a particular methodology for the detection of agglutination within one or more disposable tips. As will be readily apparent from the discussion, the inventive concepts described herein can also be suitably applied to other reaction processes in addition to blood typing to detect antigens, antibodies, proteins, viruses, and the like. In addition, such terms as "top", "bottom", "lateral", "above", "below" and the like are also used in order to provide a convenient frame of reference for use with the accompanying drawings. These terms, unless stated specifically otherwise, however, are not intended to be limiting of the present invention.

Referring to FIG. 1, a disposable probe tip 100 for the detection of particle agglutination is shown for use in the present application. The probe tip 100 is defined by three (3) adjacent interconnected internal cavities or chambers, 120, 130, 140, and 150, each of the chambers being linked by a common wall. A first input port 110 of the probe tip 100 can be connected to a pump or other means (not shown) for applying negative or positive pressure to the internal cavities of the probe tip as is known in the art. This negative or positive pressure facilitates the movement of one or more liquids within the internal cavities of the probe tip. Movement mechanisms that can be used in conjunction with a probe tip of the invention to move liquids within the probe tip 100 are described in greater detail in U.S. Publication Numbers US 2002/0076826 and US 2002/0081747, each of which are incorporated by reference in their entirety. A fluid having a predetermined density and viscosity is not necessarily required. In the herein described embodiment, the internal cavities include a sample cavity 120, a flanking cavity 130 adjacent to the sample cavity, and a detection cavity 150 that is disposed below the sample cavity 120.

FIG. 3 shows a view 320 from the position of an observer 310 looking downwardly along a primary vertical axis 104 of the probe tip at a horizontal cross section 300 there through. In this embodiment, the flanking cavity 130 forms a single trough-like structure around the perimeter of the sample cavity 120 to form a lip 240. In another embodiment, the primary vertical axis 104 of the probe tip 100 and the primary vertical axis 180 of the flanking cavity 130 combine to form an acute angle 190 of less than 90 degrees. Alternatively, the vertical axes can form an acute angle of 65 degrees or less, and preferably form an acute angle of 45 degrees or less.

Figure 4A:
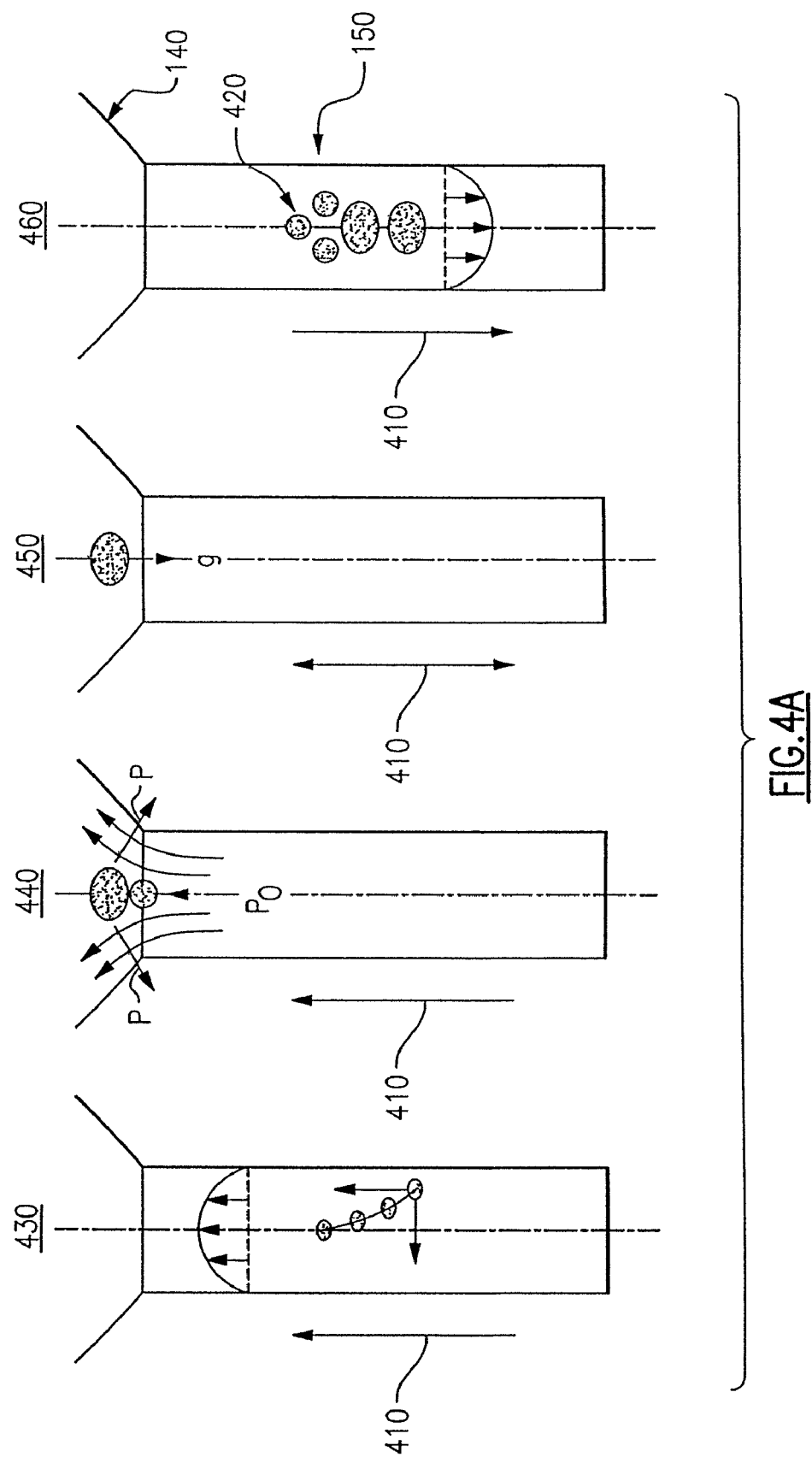
FIG. 4(a) depicts a partial sectional view of the tip of FIGS. 1-3(b), illustrating rotational mixing at a transient zone of the probe tip.
Figure 4B:
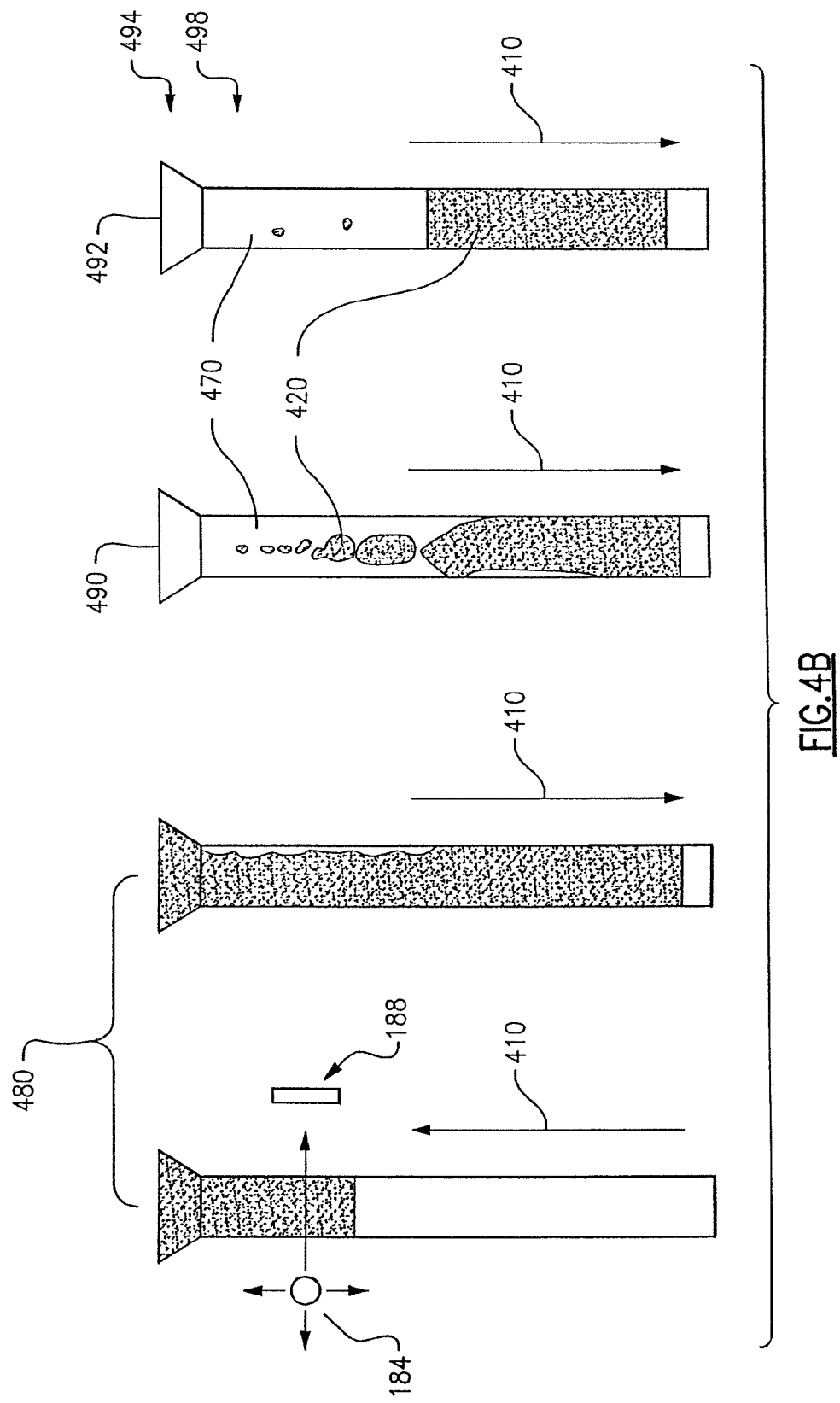
FIG. 4(b) depicts sequential views of a portion of the probe tip of FIGS. 1-4(a) illustrating the separation of agglutinated cells from non-agglutinated cells within the probe tip.
Figure 8A:
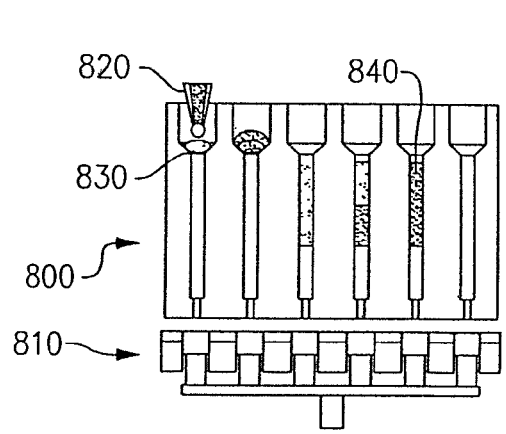
FIGS. 8(a)-8(d) illustrate sequential views of an apparatus for particle agglutination in multiple probe tips using an assembly, made in accordance with a fourth embodiment.
Figure 8B:
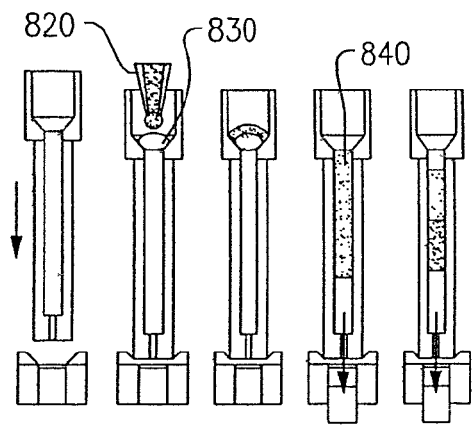
Figure 8C:
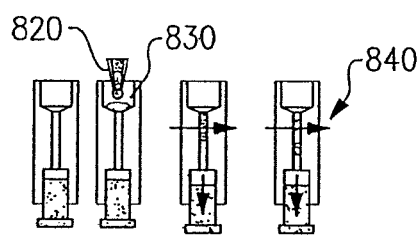
Figure 8D:
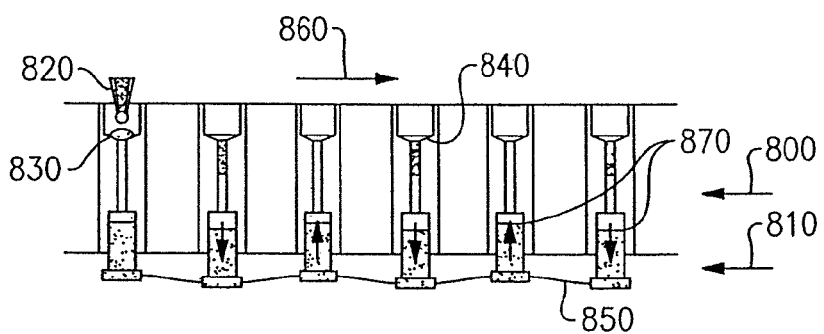

Referring again to FIGS. 1 and 2, a transition zone 140 is located between the sample cavity 120 and the detection cavity 150 and is characterized by a gradual decrease or inward taper in the internal diameter of the wall 192 of the transition zone 140 from the sample cavity 120 to the detection cavity 150. The diameter of the internal wall at the top of the transition zone 140 is therefore substantially greater than the diameter of the internal wall at the bottom of the transition zone 140. As shown in FIG. 4 and described in greater detail herein, this step structure favors the rotational mixing of fluids moving back and forth through the transition zone 140 and facilitates particle agglutination within the probe tip 100. Description of agglutination reactions in the absence of centrifugation are also disclosed in greater detail in U.S. Pat. No. 6,641,993 and U.S. Publication Numbers US 2007/0054405, US 2002/0076826 and US 2002/0081747, the contents of which are incorporated herein in the entirety.

FIGS. 1 and 2 further illustrate an emitter 184, such as a photodiode or LED, that is placed exterior to and adjacent to one wall of the detection cavity 150. Typically, particle agglutination is detected by measuring the amount of light scattering by test samples within the detection cavity 150 using techniques that are well known in the art. A sensor 188 is axially aligned in an appropriate position opposite the emitter 184 to capture the transmitted light 176. In one embodiment, the emitter 184 emits visible light and the sensor 188 measures the amount of light scattering within the detection cavity 150. A person of ordinary skill in the art will recognize that the emitter 184 could also provide electromagnetic radiation of any wavelength, depending on the method chosen to detect particle agglutination. For example, particle agglutination may result in the incorporation of a fluorophore-conjugated antibody in the agglutinate. Measurement of particle agglutination would then require the detection of fluorescence within the detection cavity 150. The emitter 184 would need to emit electromagnetic radiation 172 at a precise wavelength to excite the fluorophore-conjugated antibody within the agglutinate. The sensor 188 would then measure the amount of fluorescence 176 emitted from the agglutinate within the detection cavity 150.

The probe tip 100 can be made of any material capable of being molded into an appropriate shape such as described above. An example of a material useful for the fabrication of a probe tip as described herein is an injection-moldable plastic material such as acrylic. Preferably, the sample being analyzed does not adhere to the walls of the internal cavities of the probe tip 100 wherein these surfaces of the probe tip may be treated to avoid such adherence of the sample or reagents to the internal surfaces of the probe tip. Furthermore, the wall of the detection cavity 150 is made of material that is a transparent, clear plastic such as acrylic that permits light 172 coming from a light source 184 to traverse the detection cavity to the sensor 188. In one embodiment, the plastic of the probe tip 100 provides a transparency range for electromagnetic radiation of wavelengths between about 220 nm to 1,600 nm.

In response to the negative or positive pressure applied to the internal cavities of the probe tip 100 through the first input port 110, the test sample and/or reagents within the internal cavities of the probe tip can be aspirated or dispensed through a second port 160. In one embodiment, one or more reagents for particle agglutination may be pre-loaded in the herein described probe tip.

Referring to FIG. 2, the probe tip 100 can be centrifuged around its primary vertical axis 104. The centrifugation exerts a centrifugal force, shown by arrow 210, on particles present within the sample cavity 120 that is perpendicular to the primary axis 104. In another embodiment, the particle 200 is a magnetic particle. In the presence of a strong magnetic field, the particles 200 can move from the sample cavity 120 toward the flanking cavity 130 in response to an magnetic attractive force 210. The effect of these forces, whether they be centrifugal or magnetic in nature, on particles 200 within the sample cavity 120 is to promote the movement of the particles into the flanking cavity 130, along the outer wall 220 of the flanking cavity and eventual collection as a pellet 230 at the bottom of the flanking cavity 130. The acute angle 190 between the primary axis 104 of the probe tip 100 and the primary axis of the flanking cavity 130 forms a lip 240 that further facilitates the capture of the particles to the flanking cavity.

With the foregoing structural description of a suitable probe tip 100, a method is now described with respect to agglutination reactions for blood typing. It will be readily apparent to one of sufficient skill and as described in greater detail that the following description is exemplary and therefore, there is potential to use antigen carriers other than red blood cells.

Referring to FIGS. 5A-5K, the individual steps required for the analysis of an indirect Coomb's agglutination test are herein depicted using the probe tip 100 of FIGS. 1-3(b). The indirect test consists of mixing serum potentially containing an antibody with a suspension of red cells of known blood type, adding anti-human immunoglobulin (Coomb's reagent) and then testing for agglutination of the red blood cells.

Blood taken from a patient is first treated with heparin, or equivalent polyanion, to inhibit coagulation. The blood is then centrifuged. The supernatant containing the serum is collected and incubated with a donor's red blood cells for 1-60 minutes at 37 degrees Celsius.

Referring to FIG. 5A, the port 160 of the probe tip 100 is first immersed in a sample 540 containing a patient's serum and the donor's red blood cells. A pump (not shown) attached to the opposite input port 110 then aspirates air, shown by arrow 510, from the internal volume of the probe tip 100 formed by cavities 120, 130 and 150. The displacement of air 510 out of the probe tip creates a negative pressure within the tip that promotes the movement 520 and 530 of sample 540 into the cylindrical lower chamber 150 of the probe tip. In one embodiment, an aliquot of between 0.1 to 50 microliters of sample 540 are aspirated. In a preferred embodiment, from 0.1 to 10 microliters of sample 540 are aspirated into the interior cavity 150 of the probe tip 100.

As shown in FIG. 5B-5D, the port 160 of the probe tip 100 is removed from the sample 540. The pump attached to port 110 aspirates air 510 from the probe tip, which in turn moves the aspirated sample 560 in the direction 570 through the interior volume of the probe tip 100 from cavity 150 to the sample cavity 120 and the adjacent flanking cavity 130. The port 110 is then closed to ensure the sample 580 remains in the sample cavity 120.

In one embodiment, the probe tip 100 is then centrifuged by rotating the tip, shown by arrow 590, around its primary vertical axis 104. Centrifugation generates a centrifugal force, shown by arrows 554, within the sample chamber 120 that is substantially perpendicular to the primary vertical axis 104. As illustrated in FIG. 5E, the centrifugal force 554 acts on the coated red blood cells to move them from the sample chamber 120, along the outer wall of the flanking cavity 220 to form a pellet 558 at the bottom of the flanking cavity and separates them from the rest of the sample (see also FIG. 2(b)). As depicted in FIG. 5F, the application of positive pressure 568 through the port 110 then produces a movement, shown by arrow 562, that expels the sample supernatant 566 from the probe tip 100.

Referring to FIG. 5G-H, the port 160 of the probe tip 100 is then immersed in a reagent for agglutination, i.e., anti-human immunoglobulin 578 (Coomb's reagent). Application of negative pressure, shown by the arrow 572, through port 110 drives the aspiration of the anti-human immunoglobulin 578 from the lower cavity 150 of the probe tip to the sample and flanking cavities 120 and 130. Application of alternating positive and negative pressure shown by the arrows 586 through port 110 facilitates the resuspension of the red blood cell pellets 558 at the bottom of the flanking cavity 130. Positive pressure through the port 110 then moves the resuspension to the transition zone 140. As shown in FIG. 5I, the application of alternating positive and negative pressure 592 through the port 110 promotes the rotational mixing of the red blood cells 588 with the anti-human immunoglobulin 584 as the resuspension passes back and forth, as shown by arrow 594, through the transition zone 140 (see also FIG. 4). In one embodiment, fluids are moved through the transition zone in 25 µl increments either up or down followed by a pause of variable duration as described below.

| 25 µl displacement | Displacement Time (seconds) |
|---|---|
| Up | 5 |
| Down | 20 |
| Up | 10 |
| Down | 30 |
| Up | 15 |
| Down | 40 |
| Up | 20 |
| Down | 40 |
| Up | 25 |
| Down | 35 |

Finally, as shown in FIGS. 5J and 5K, application of positive pressure shown by arrow 596 through the port 110 pushes the cell suspension to the detection cavity 150 where cell agglutination is measured. Light 598 emitted from a light source 184, level with the upper half of the detection cavity, traverses the cell suspension and is captured by a sensor or photodetector 188. Methods of photodetection are disclosed in greater detail in U.S. Publication Number US 2007/0054405, the contents of which were previously incorporated herein by reference in its entirety. Two scenarios are possible. If the cell suspension 595 is uniform, there is no agglutination and the light absorption is high. The absence of agglutination indicates a patient's serum fails to react with the donor's red blood cells and that the donor is compatible with the patient for blood transfusion purposes (see FIG. 5J). If, however, the cells form clumps 597 that sink under gravity to the bottom of the detection cavity 150, light absorption is low. The presence of agglutination indicates the patient's serum contains one or more antibodies that can react with the donor's red blood cells. The donor's blood is therefore not suitable for blood transfusion into the patient.

A person of ordinary skill in the art will recognize that the described embodiment can be altered in a number of ways and still fall within the intended scope of the application. For example, the probe tip described herein can be used in a series of two or more probe tips. For example, a first probe tip may be used to collect heparinized patient blood and pellet the cellular fraction of the blood into the flanking cavities by centrifugation. The serum supernatant is then dispensed from the sample cavity into a receptacle from where it can be processed in a second probe tip as described above. In another embodiment, the probe tip may aspirate one or more reagents for agglutination.

In yet another embodiment, other particles such agarose or latex beads and the like may be used instead of cells. A number of ligands are known that bind immunoglobulin molecules and may be covalently coupled to the particles, for example Protein A, Protein G, Protein A/G and KappaLock™. Protein G is a particularly preferred ligand for use in assays where IgG immunoglobulins are used or tested for. One reason that Protein G is preferred is that it has a greater affinity than Protein A for most IgG immunoglobulins. Protein G also binds with a significantly greater affinity than Protein A to certain subclasses of IgG, e.g., human IgG3, mouse IgG1 and rat IgG2a. Protein G does not bind to human IgM, IgA and IgD.

Protein G is a bacterial cell wall protein isolated and purified from group G streptococci. Protein G binds to mammalian IgG immunoglobulins through their Fc portion. Because Protein G only binds the Fc portion of IgG immunoglobulins, the antibody portion of the immunoglobulin remains available for reaction with its corresponding antigen, yet the immunoglobulin remains bound to the particle. Native Protein G has been sequenced by DNA analysis. From the DNA analysis, two IgG binding domains and sites for albumin and cell surface binding have been identified.

ImmunoPure® Immobilized Protein G is a commercially available particle product having Protein G immobilized on the surface of agarose gel bead particles. This product is available from Pierce of Rockford, Ill. The immobilized Protein G has been genetically engineered to remove the albumin and cell surface binding regions and thereby minimize the binding of anything other than immunoglobulins. ImmunoPure® Immobilized Protein G consists of a recombinant Protein G covalently linked (glutaraldehyde activation of the beads) to cross-linked 6% beaded agarose. The material is supplied in a 50% slurry. The material can bind 11 mg of human IgG per ml of gel.

Protein A is a cell wall component produced by several strains of Staphylococcus aureus. Protein A is capable of specifically binding the Fc region of immunoglobulin molecules, especially IgG. The Protein A molecule has four high affinity binding sites that are capable of interacting with the Fc region from IgG of several species. Protein A interacts with some IgG subgroups and not with others. For example, human IgG1, IgG2 and IgG4 bind strongly while IgG3 does not bind. And, there are also some instances in which monoclonal antibodies do not bind to Protein A.

Immobilized Protein A is also available commercially from Pierce Biotechnology, Inc. Rockford, Ill. 61105 U.S.A. This immobilized Protein A is a highly purified Protein A, covalently coupled to crosslinked beaded agarose. The typical binding capacity for this immobilized Protein A is 12-15 mg of human IgG per milliliter of gel.

Protein A/G is a genetically engineered protein that combines the IgG binding profiles of both Protein A and Protein G. Protein A/G is a gene fusion product secreted from a non-pathogenic form of Bacillus. This genetically engineered Protein A/G is designed to contain four Fc binding domains from Protein A and two from Protein G.

Protein A/G binds to all human IgG subclasses. In addition, it binds to IgA, IgE, IgM and to IgD but to a lesser extent to IgD. Thus, Protein A/G may be a preferred ligand in tests for or tests using non-IgG class immunoglobulins.

Pierce also offers an immobilized Protein A/G covalently coupled to beaded agarose under the trade name ImmunoPure® Immobilized Protein A/G.

KappaLock™ is a universal kappa light chain binding protein available from Aaston, Inc., 12 Falmouth Road, Wellesley, Mass. It has been genetically engineered from the DNA of a strain of Peptostreptococcus. This protein binds to the kappa region of the light chain of all antibody types. KappaLock™ has been genetically engineered to delete the albumin and cell wall binding regions of the naturally occurring bacterial protein. The resultant engineered protein has four antibody binding domains and specifically does not bind to heavy chains or to the Fc region of immunoglobulins. Because kappa light chains are shared among different classes of antibodies, KappaLock™ will bind to antibodies having a kappa light chains regardless of heavy chain class.

KappaLock™ may be immobilized on various supports, particularly on agarose beads. Immobilized KappaLock™ will capture mouse IgG, rabbit IgG, human IgG, human IgA and human IgM.

All of the preferred ligands may be covalently bound to a solid-phase matrix such as agarose beads (e.g., Sepharose Pharmacia) using known techniques, for example as described by Heam et al., Methods in Enzymology Vol. 35:102-117 (1987). Generally, the beads are first activated by a chemical agent, such as glutaraldehyde, carbonyldiimidizole, cyanogen bromide hydroxysuccinimide, tosyl chloride or the like. The chosen ligand is then covalently attached to the beads, resulting in an extremely stable linkage of the ligand to the support.

In yet another embodiment, the particles may be bound by bacteriophage expressing an antibody on the surface of the bacteriophage, see, for example, U.S. Pat. No. 6,979,534, the contents of which are hereby incorporated by reference in their entirety. U.S. Pat. No. 6,979,534 teaches a method of identifying an antigen-bearing moiety on a cell comprising providing a mixture comprising a population of cells and a population of bacteriophage expressing a known first antibody on the surface of the bacteriophage. The presence of the antigen-bearing moiety on the cell is indicated by binding of the first antibody to at least two of the cells causing the bacteriophage to also bind to the at least two of the cells, adding a second antibody specific for the bacteriophage. The presence of agglutination identifies the antigen-bearing moiety as being an antigen-bearing moiety specific for the first antibody.

According to another embodiment, the beads are magnetic beads. Magnetic particles can be captured to the flanking cavity and separated from the rest of the sample as described above by simply deploying a powerful magnet adjacent to the flanking cavity in the absence of centrifugation. Many methods are known in the art where cells can be rendered magnetic for purposes of cell separation and the like. For example, cells can be incubated with biotinylated antibodies or other ligand-binding molecules that are specific for a surface antigen, characteristic of a particular cell type. Addition of streptavidin-conjugated magnetic beads (Invitrogen/Dynal Biotech) then bind to the biotinylated antibodies and thereby render the cells magnetic and hence amenable to cell separation using a magnetic field. The description of controlled transport of magnetic beads is disclosed in U.S. Pat. No. 7,217,561, the contents of which is hereby incorporated herein in its entirety.

Cells used in the invention may also be tagged using labeled antibodies known in the art. For example, the labeled antibodies may a fluorophore-conjugated antibody. Agglutination can then be monitored by the detection of fluorescence emitted from agglutinated cells.

The use of pneumatic means, capable of applying negative (vacuum) or positive (pumping) pressure, for the displacement of liquids within the internal volume of a probe tip used herein is also contemplated by the present disclosure.

FIG. 6(a) depicts a probe tip according to a second embodiment having an interior volume consisting of a sample cavity 610, a transition zone 620, a detection cavity 630 and a displacement cavity 640 respectively, all of which are interconnected. FIG. 6 (b) further depicts a piston 660 which is movably disposed within the displacement cavity 640. Referring to FIGS. 6 (c) to (d), the sample 650 to be analyzed is essentially added to a reagent for particle agglutination 670 in the sample cavity 610. The outward movement 690 of the piston 660 within the displacement cavity 640 causes a negative pressure within the internal volume of the probe tip and the subsequent movement 654 of the sample and the reagents into the detection cavity 630. The stroke movements 658 of the piston into and out of the displacement cavity 640 cause the analogous back and forth movement of the liquids through the transition zone 620 and thereby promotes rotation mixing 666 of these fluids. A sequence of movements that may be used for the rotational mixing in the transition zone 620 is described in detail in the Example below.

The withdrawal 690 of the piston 660 in the displacement cavity 640 aspirates the particle suspension into the detection zone 630 where the agglutinated particles sediment by gravity and the flow field during the oscillation movement. The amount of light absorption 598 is then determined using an emitter 184 and sensor 188 and in which an absence of light absorption is indicative of particle agglutination.

Figure 10:
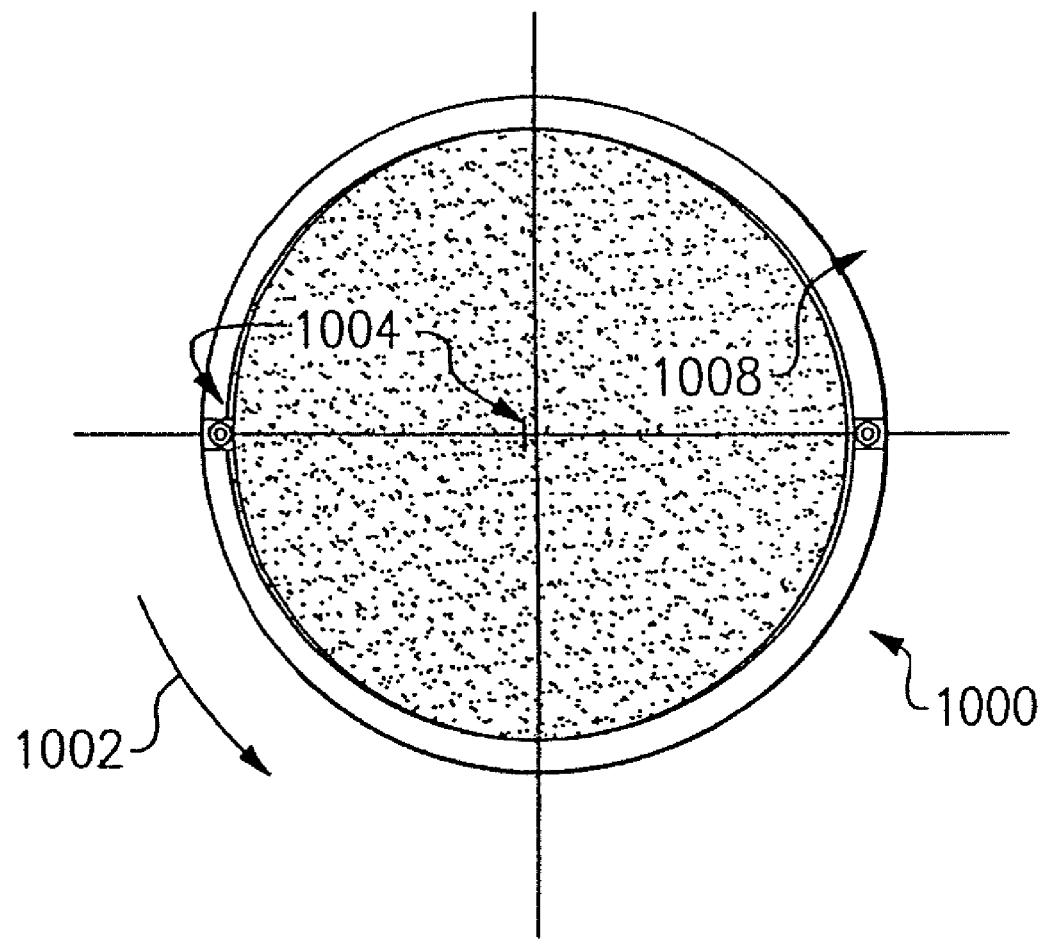
FIG. 10 shows a cross sectional view of an incubator disc that is off center.

In one exemplary embodiment, the movement of the piston 660 is linked to the rotation or circular oscillation by way of attachment of the piston to the drive mechanism of a rotatable apparatus; for example, an incubator (see FIG. 10). The incubator includes at least one circular rotor having a plurality of slots that are sized to retain probe tips such as the foregoing. The drive mechanism can be via a belt drive or a gear drive, by way of example in which the drive mechanism is controlled relative to the rotation of the rotor. As the rotor rotates, the piston moves back and forth, providing a force that drives the oscillation of fluid inside the tip. As a result of the effects of the flow field and gravity, any large agglutinated structures are transported to the bottom of the tip. On the contrary, in a negative reaction, there is no agglutination and a near homogeneous mixing is observed. The amount of agglutination can then be accurately assessed using an optical source and sensor to measure the absorbance in the detection chamber 150.

FIG. 7 illustrates a probe tip assembly configuration that is amenable to automation. FIG. 7(a) shows a series of 6 probe tips 782 that can be connected to a pump (FIG. 7(b)) either through a proboscis disposed at the top of each probe tip 750 (see FIG. 7(a)), to a series of pistons 780 (see FIG. 7(f)) or by means of a deformable membrane 778 (see FIG. 7 (g)) disposed at the bottom of the probe tips. The probe tips may be pre-loaded with reagents 730 for particle agglutination and sealed with a adhesive sheet. The sample may be loaded from multiwell plates having a plurality of wells. FIGS. 7(c)-7(e) and FIGS. 8(a)-8(b) sequentially depict the tip as agglutination reactions are accelerated in a series of probe tips. In one embodiment, a drive belt 850 is used for the coordinated movement of the series of pistons. Computer means and its programming for the automation of the pipetting steps, movement of the pistons, movement of the microtiter plates and movement of the probe tips are also contemplated by this invention. An automated platform may also comprise a centrifuge for the centrifugation of a plurality of probe tips as defined herein or means for the application of a magnetic field according to the requirements of the agglutination assay.

The disclosure herein also provides for a kit format which comprises a package unit having one or more probe tips of the subject invention and in some embodiments includes containers of various reagents. The kit may also contain one or more of the following items: reagents for agglutination including, but not limited to antibodies (for example: Coomb's reagent), buffers, instructions, and controls. Kits may include containers of reagents mixed together in suitable proportions for performing the methods in accordance with the invention. Reagent containers preferably contain reagents in unit quantities that obviate measuring steps when performing the subject methods. Kits may further comprise probe tips pre-loaded with reagents for agglutination assays.

The invention will now be further illustrated with reference to the following example. It will be appreciated that what follows is by way of example only and that modifications to detail may be made while still falling within the intended scope of the invention.

EXAMPLE

Indirect and Direct Coomb's Test in a Probe Tip

A single capillary with a step in the flow channel was used to perform blood grouping and antibody screening (direct and indirect Coomb's testing, see FIGS. 9(a)-9(d)). First, a glass capillary 992 was linked to a short section of tubing 996 to create a tip with a step. The capillary had a volume of 25 µl with a length of 54 mm. The tubing 996 had a diameter of 3 mm and a length of 6 mm. A Hamilton syringe (not shown) was used to drive fluid flow. The following reagents were used in the assays:

| Reagent | Product Code (Ortho-Clinical Diagnostics, Inc.) |
|---|---|
| Anti-A BioClone ® | 711220 |
| ORTHO ® Anti-IgG Green | 716760 |
| Antibody Enhancement Solution | 718780 |
| ORTHO ® Anti-Kell | 715150 |
| AFFIRMAGEN ® (3%) | 719210 |
| SELECTOGEN ® (3%) | 719610 |
| ORTHO ® Coombs Control | 719810 |

Anti-A BioClone comprises ABO blood grouping reagents. ORTHO® Anti-IgG Green contains Anti-Human Globulin Reagents. ORTHO® Anti-Kell contains blood grouping reagents and AFFIRMAGEN, SELECTOGEN and ORTHO® Coombs Control are red blood cell reagents.

33% heparinized blood was centrifuged to remove some serum so that the blood HCT became about 30 to 40% blood HCT. All the experiments were performed at room temperature except for cell coating, which was performed at 37 degrees Celsius.

Direct Coomb's Test

The following reagents were aspirated into the capillary (total volume of 10 microliters):
  Direct I Test (FIG. 9(a)):
    Anti-A BioClone® and AFFIRMAGEN® A cell (Positive reaction) or Anti-A BioClone® and AFFIRMAGEN® B cell (negative reaction) OR Direct II Test (FIG. 9(b)):

ORTHO® Anti-IgG Green and ORTHO® Coombs Control (Positive control) or ORTHO® Anti-IgG Green and AFFIRMAGEN® A cell (negative control)

Back and forth movements over the step were then achieved by moving the plunger within the Hamilton syringe by 25 μl increments. Each movement was followed by a pause of variable duration as outlined in Table I (columns Direct I and II). At the completion of the protocol, the cell suspension was drawn down into the capillary proper for visual inspection. With positive reactions (982 and 986), the agglutinated cell complexes sedimented by gravity within the capillary whereas in negative reactions (984 and 990) the cells remained in suspension (see FIGS. 9 (a)-9 (b)). The amount of agglutination was quantitated by the measurement of the absorption of light (930) within the top half of the capillary tube (see FIG. 9(c)).

Figure 9A:
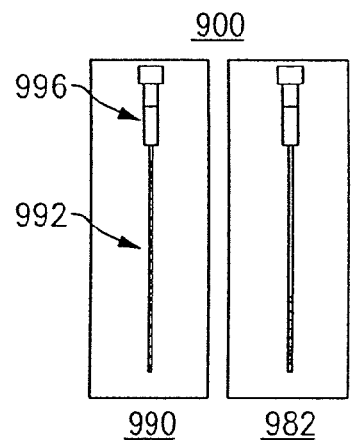
Figure 9B:
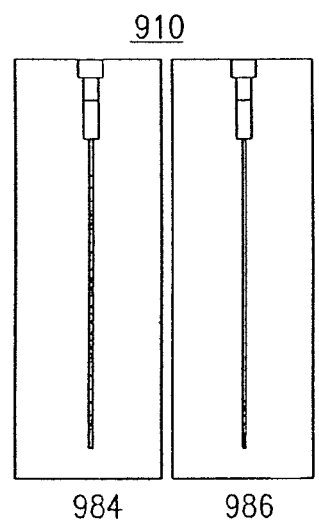
Figure 9C:
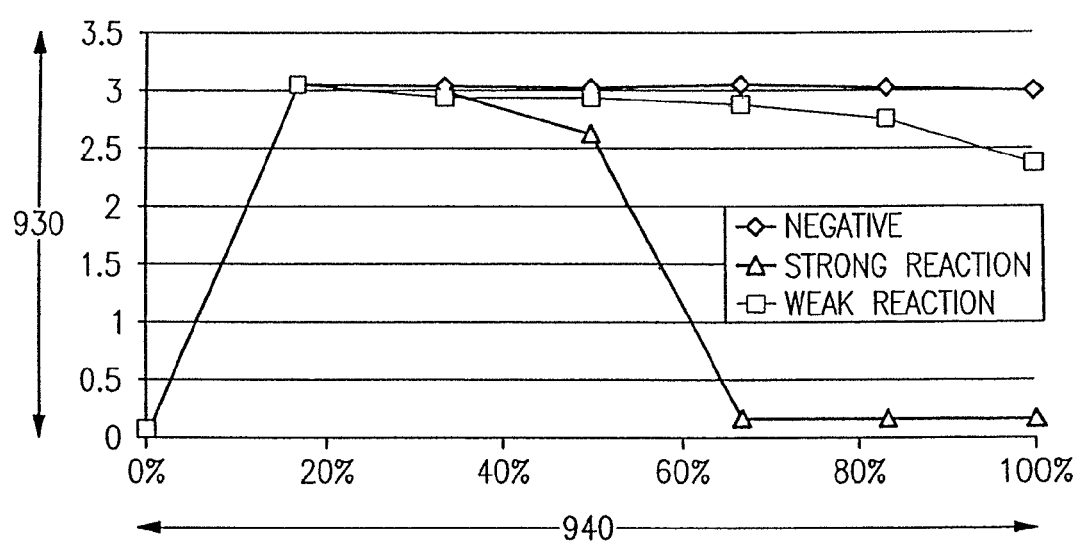
Figure 9E:
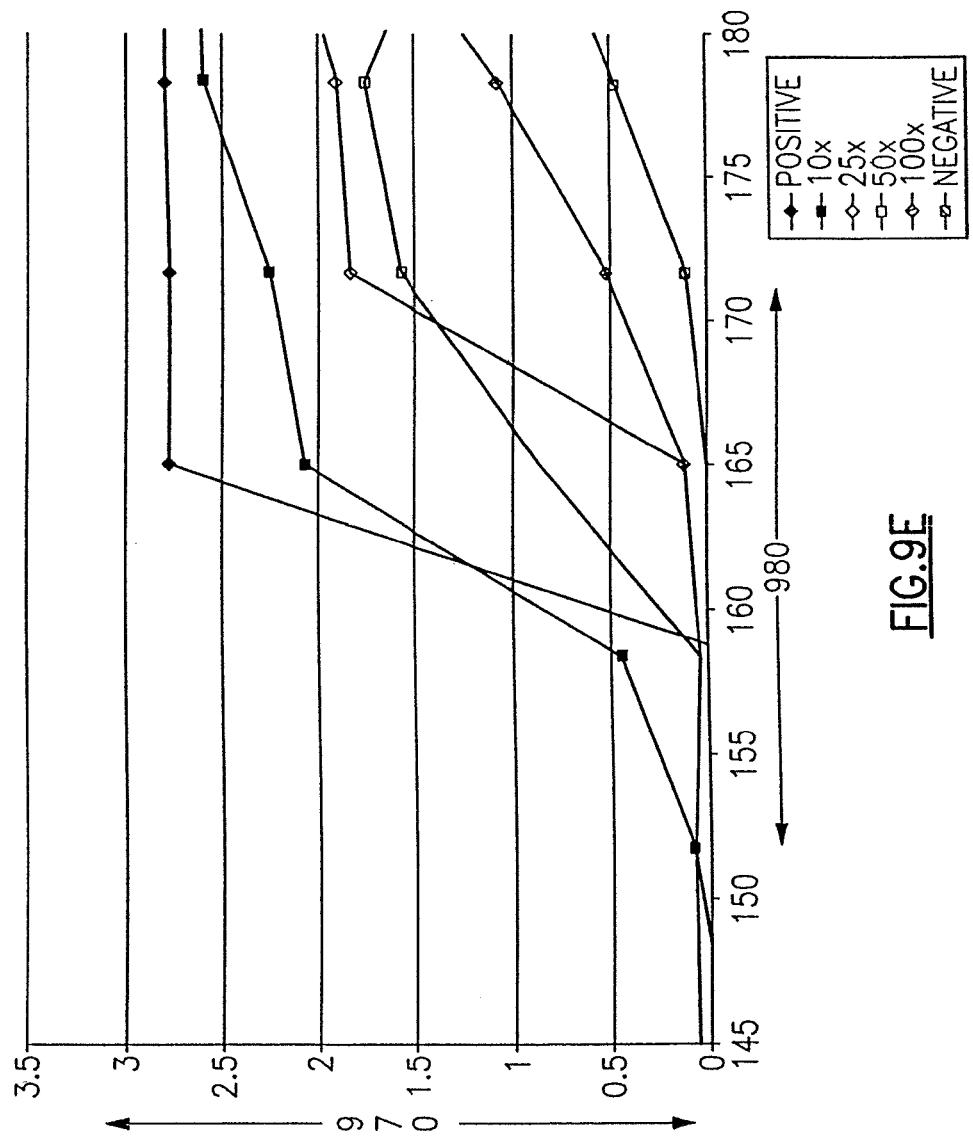
Figure 9D:
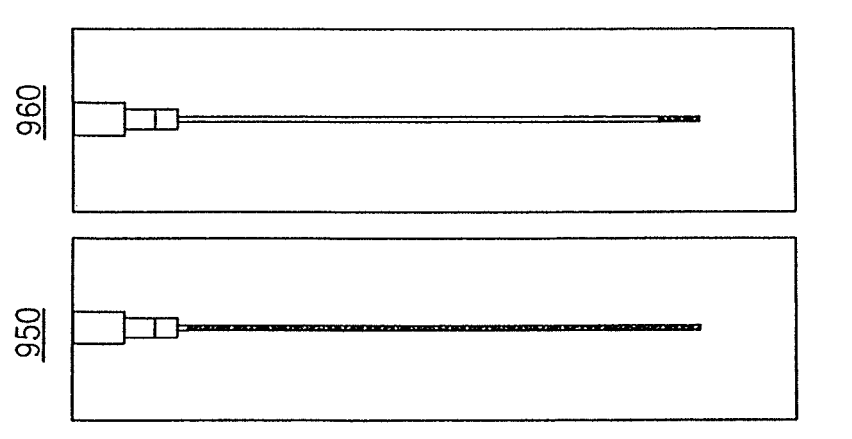

Indirect Coomb's Test (FIGS. 9(d) and 9(e))

ORTHO® Anti-Kell was mixed with SELECTOGEN® Cell (K+) and the mixture was incubated for 30 minutes at 37° C. temperature. Similarly, ORTHO® Anti-Kell was mixed with SELECTOGEN® Cell (K−) allowed to incubate 30 minutes at 37° C. temperature. Saline was then added and the mixture was centrifuged to separate the cells from the fluid. The process was repeated three times. The washed cells were resuspended in saline.

ORTHO® Anti-IgG Green was then added to the coated SELECTOGEN® Cell (K+) for the positive reaction (960) or SELECTOGEN® Cell (K−) for the negative control (950) and aspirated into the capillary ((total volume of 10 microliters). Back and forth movements in 25 μl increments over the step was achieved by moving the plunger within the Hamilton syringe. Each movement was followed by a pause of variable duration as outlined in (see Table I, column Indirect). At the completion of the protocol, the cell suspension was drawn down into the capillary proper for visual inspection. With positive reactions (960), the agglutinated cell complexes sedimented by gravity within the capillary whereas in negative reactions (950), the cells remained in suspension (see FIG. 9 (d)). The amount of agglutination was also quantitated by the measurement of the absorption of light 970 within the top half of the capillary tube (see FIG. 9(e)). 10×, 25×, 50× and 100× indicates the dilution of the sample.

TABLE I

| 25 ml displacement | Direct I | Direct II | Indirect |
|---|---|---|---|
| | Displacement Time (seconds) | | |
| Up | 5 | 5 | 5 |
| Down | 20 | 20 | 20 |
| Up | 10 | 10 | 10 |
| Down | 30 | 30 | 30 |
| Up | 15 | 15 | 15 |
| Down | 40 | 40 | 40 |
| Up | Stop | Stop | 20 |
| Down | | | 40 |
| Up | | | 25 |
| Down | | | 35 |

Parts List for Figs. 1-10
100 Probe tip
104 Primary vertical axis of probe tip
110 Input port
120 Sample cavity
130 Flanking cavity
140 Transition zone
150 Detection cavity
160 Input port
170 Wall of probe tip
172 Electromagnetic radiation
176 Transmitted light
180 Primary vertical axis of flanking cavity
184 Emitter or light source
188 Sensor or photodetector
190 Angle between primary vertical axis of probe tip and primary vertical axis of flanking cavity
192 Inner wall—transition zone
200 Particle.
210 Direction force
220 Outer wall flanking cavity
230 Pellet of particles
240 Lip
300 Position of cross section of probe tip
310 Position of observer looking down at cross section through probe tip
320 View of cross section 320 from the position of the observer 310
410 Vertical movement of fluids
420 Agglutinated particles
430 Shear migration
440 Flow field
450 Gravity
460 Velocity field
470 Supernatant
480 Cycle 1
490 Cycle 2
492 Cycle 3
494 Transition zone
498 Detection cavity
510 Air being aspirated out of the internal cavities of the probe tip through the port 110
520 Aspiration of sample
530 Direction—reagent movement
540 Sample
550 Aspiration of air
554 Direction of centrifugal force
556 Supernatant of sample
558 Pellets of particles
560 Sample aspirated
562 Direction
566 Sample supernatant
568 Positive pressure
570 Direction of the movement of liquids
572 Negative pressure
574 Reagent for agglutination.
578 Aspiration of reagents
580 Sample
582 Direction of the movement
584 Reagents for agglutination
586 Application of negative or positive pressure
588 Rotational mixing of the resuspended cells
590 Rotation of probe tip
592 Application of positive or negative pressure
594 Aspiration or expulsion of air
595 Resuspended non-agglutinated cells
596 Application of positive air pressure
597 Agglutinated cells
598 Path of visible light
610 Sample cavity
620 Transition zone
630 Detection cavity
640 Displacement cavity
650 Sample
654 Displacement of mixture
658 Arrow 660 Piston
662 Back and forth movement of sample and reagents for particle agglutination
666 Rotational mixing of sample and reagents
670 Reagent
680 Mixture of sample and reagents
690 Movement of piston
710 Proboscis insertion
720 Step
730 Reagent
740 Airgap
750 Hole for proboscis
760 Reagent pre-loaded
770 Dispensed sample
780 Mixed sample and reagent
778 Deformable membrane
780 Piston
782 Probe tips
790 Agglutination separation
800 Assembly of probe tips
810 Assembly of pistons
820 Sample
830 Reagent(s) for agglutination
840 Mixture of sample and reagents for agglutination
850 Drive belt
860 Tip-cuvette moving direction
870 Direction of piston movement
900 Direct agglutination (ABO)
910 Direct Antiglobulin Case (IgG)
920 Absorbance as function of location
930 Absorbance
940 Liquid column position (from bottom up)
950 Negative selectogen cell (−)
960 Positive Selectogen Cell (+)
970 Integral of Absorbency
980 Time in seconds
982 Positive (Type A)
984 Negative (Type A)
986 Positive (Coomb's reagent)
990 Negative (TypeB)
992 Capillary
996 Tubing
1000 Incubator disc
1002 Direction of oscillation movement
1004 Off center discs driving pumps in tips
1008 Light While this invention has been particularly shown and described with references to preferred embodiments thereof, it will be understood by those skilled in the art that various changes in form and details may be made therein without departing from the intended scope of the invention encompassed by the following appended claims.

The invention claimed is:

1. An apparatus for the detection of agglutination reactions within at least one probe tip, said apparatus comprising at least one holder configured for the placement of at least one probe tip, said at least one probe tip comprising:
   i. a first port in fluid communication with an internal volume of a probe tip;
   ii. a sample cavity of said internal volume in fluid communication with said first port;
   iii. a detection cavity of said internal volume configured for the detection of agglutinated particles within the sample, wherein said detection cavity is in fluid connection with said sample cavity;
   iv. a transition zone of said internal volume disposed between said sample cavity and said detection cavity, said transition zone being configured for rotational mixing of the sample moving back and forth through said transition zone between said detection cavity and said sample cavity through agitation thereof;
   v. a second port in fluid connection with said detection cavity, said port being configured to permit reagents and sample from said apparatus to be aspirated into or dispensed from said internal volume of said probe tip, and
   vi. a third port, said third port being laterally disposed relative to second port and in fluid communication with a displacement cavity of said probe tip and wherein said displacement cavity is sized to receive a piston, said piston being laterally movable within said laterally disposed third port to cause movement of fluids within said probe tip.

2. The apparatus of claim 1, wherein the volume of said displacement cavity changes with the movement of the piston in said displacement cavity.

3. The apparatus of claim 1, wherein the lateral back and forth movement of said piston within said displacement cavity displaces a column of air that in turn exerts a back and forth force against the sample and the reagents through said transition zone of said probe tip.

4. The apparatus of claim 1, wherein the lateral back and forth movement of said piston within said displacement cavity of said tip is coordinated with the rotation of said probe tip within a rotor about the axis of said rotor.

5. The apparatus of claim 1, further comprising means for the detection of agglutination in said probe tips.

6. The apparatus of claim 1, wherein said reagents are provided for promoting agglutination of said sample, said reagents comprising one or more ligand-binding molecules.

7. The apparatus of claim 1, wherein said reagents are provided for promoting agglutination of said sample, said reagents comprising microspheres bound by ligand-binding molecules.

8. The apparatus of claim 6, wherein said ligand-binding molecules are antibodies.

9. The apparatus of claim 1, wherein said reagents are provided for promoting agglutination of said sample, said reagents comprising Coomb's reagent.

10. The apparatus of claim 1, wherein said reagents comprise red blood cells of a known blood group.

11. The apparatus of claim 5, wherein agglutinated particles are separated from the remainder of the sample following reaction by centrifugation or by separation in a magnetic field.

12. The apparatus of claim 1, wherein said apparatus comprises a plurality of said holders for the placement of a plurality of said probe tips.

* * * * *